United States Patent [19]

Todaro

[11] Patent Number: 4,863,899

[45] Date of Patent: Sep. 5, 1989

[54] BIOLOGICALLY ACTIVE POLYPEPTIDES

[76] Inventor: George J. Todaro, 1940 15th Ave. East, Seattle, Wash. 98112

[21] Appl. No.: 53,249

[22] Filed: May 22, 1987

Related U.S. Application Data

[60] Division of Ser. No. 777,016, Sep. 17, 1985, Pat. No. 4,861,561, which is a continuation-in-part of Ser. No. 598,136, Apr. 12, 1984, abandoned, which is a continuation-in-part of Ser. No. 492,751, May 9, 1983, abandoned.

[51] Int. Cl.$^4$ ............................................. A61K 37/02
[52] U.S. Cl. .......................................... 514/9; 514/10; 514/11; 514/12; 514/13; 514/14
[58] Field of Search .................. 530/324, 327; 514/11, 514/9, 10, 12, 13, 14

[56] References Cited

U.S. PATENT DOCUMENTS

| | | | |
|---|---|---|---|
| 4,287,185 | 9/1981 | Toyoshima et al. | 424/177 |
| 4,428,942 | 1/1984 | Rivier et al. | 424/177 |
| 4,443,434 | 4/1984 | Lien | 424/177 |
| 4,485,101 | 11/1984 | Coy et al. | 424/177 |
| 4,650,787 | 3/1987 | Schally et al. | 514/11 |
| 4,686,283 | 8/1987 | Nestor, Jr. et al. | 530/327 |
| 4,742,003 | 5/1988 | Derynck et al. | 435/68 |
| 4,749,683 | 6/1988 | Murphy et al. | 514/2 |

FOREIGN PATENT DOCUMENTS

| | | |
|---|---|---|
| 154434 | 9/1985 | European Pat. Off. |
| 0190018 | 8/1986 | European Pat. Off. |
| 59-21605 | 8/1984 | Japan. |
| 84/01106 | 3/1984 | PCT Int'l Appl. |
| 85/02198 | 5/1985 | PCT Int'l Appl. |
| WO86/02650 | 5/1986 | PCT Int'l Appl. |

OTHER PUBLICATIONS

Rivier, J. et al., *J. of Medicinal Chem.*, 18(2), 123–126 (1975).
von Heijne, G. et al., *Proc. Natl., Acad. Sci.*, 85 3363–3366 (1988).
Heimbrook, D. et al., *J. of Biol. Chem.*, 263(15), 7016–7019 (1988).
Brody, R. et al., *ICSU Short Reports* 8, 105, IRL Press (1988).
Sykes, B. et al., *J. Cell. Biochem.*, Supplement 12A, 178 (1988).
Harkins, R. et al., *J. Cell. Biochem.*, Supplement 12A, 81, (1988).
Sporn, M. et al., *N. Eng. J. Med.*, 15, 878–880 (1980).
Todaro, G. et al., *J. of Supramolecular Structure and Cell. Biochem.*, 15, 287–301 (1981).
DeLarco, J. et al., *J. Biol. Chem.*, 255(8), 3685–3690 (1980).
Ozanne, B. et al., *J. Cell. Physiol.*, 105, 163–180 (1980).
Ibbotson, K. et al., *Science*, 221, 1292–1294 (1983).
Marquardt, H. et al., *J. Biol. Chem.*, 256(13), 6859–6865 (1981).
Marquardt, H. et al., *Proc. Natl. Acad. Sci. U.S.A.*, 80 4684–4688 (Aug. 1983).
Twardzik, D. et al., *Virology*, 124, 201–207 (1983).
Gray, A. et al., *Nature*, 303, 722–725 (1983).
Derynck, R. et al., *J. Biol. Chem.*, 261(10), 4377–4379 (1986).
Roberts, A. et al., *Proc. Natl. Acad. Sci. U.S.A.*, 78(9), 5339–5343 (1981).
DeLarco, J. et al., *J. Cell. Physiol.*, 109, 143–152 (1981).
Derynck, R. et al., *Cell*, 38, 287–297 (Aug. 1984).
Wharton, J. et al., *Cell*, 43, 567–581 (1985).
McMullen, B. et al., *J. Biol. Chem.*, 260(9), 5328–5341 (1985).
Sherwin, S. et al., *Cancer Res.*, 43, 403–407 (1983).
Lee, D. et al., *Nature*, 313(6002), 489–491 (1985).
Roberts, A. et al., *Proc. Natl. Acad. Sci. U.S.A.*, 77(6), 3494–3498 (1980) [CA 93: 111935y (1980)].
Todaro, G. et al., *Proc. Natl. Acad. Sci. U.S.A.*, 77(9), 5258–5262 (1980) [CA 93:219155h (1980)].
Marquardt, H. et al., *J. Biol. Chem.*, 257(9), 5220–5225 (May 10, 1982).
Twardzik, D. et al., *Science*, 216, 894–897 (May 21, 1982).
Pike, L. et al., *J. Biol. Chem.*, 257(24), 14628–14631 (Dec. 25, 1982).
Venkatesan, S. et al., *J. Virology*, 44(2), 637–646 (1982).
Linsley, P. et al., *Proc. Natl. Acad. Sci. U.S.A.*, 82, 356–360 (1985).

*Primary Examiner*—Delbert R. Phillips
*Attorney, Agent, or Firm*—Karen Babyak Dow; Al A. Jecminek

[57] ABSTRACT

Novel biologically active polypeptides, including a new class of transforming growth factor (TGF) polypeptides, which exhibit cell growth promoting properties are disclosed, as well as a process for isolating the TGF polypeptides from both human and murine cell lines in homogeneous form. Also disclosed are antigenic oligopeptides derived from the TGF polypeptides and antibodies raised therefrom which have application in the detection and treatment of malignancies and oligipeptides which have the ability to bind with cellular growth factor receptors and thus to interfere with transformation of certain cell lines into a cancerous state. Compositions and methods based on the disclosed peptides for detection and treatment of cancer and other proliferative diseases and for cell or tissue growth associated treatment, e.g., wound healing, ulcer therapy and bone loss are also described.

44 Claims, No Drawings

BIOLOGICALLY ACTIVE POLYPEPTIDES

This application is a divisional application of co-pending application Ser. No. 777,016, filed Sept. 17, 1985, now U.S. Pat. No. 4,816,561, which was a continuation-in-part application of then copending application Ser. No. 598,136, filed Apr. 12, 1984, now abandoned, which was a continuation-in-part application of then co-pending Ser. No. 492,751, filed May 9, 1983, now abandoned.

BACKGROUND OF THE INVENTION

1. Field of the Invention

This invention relates to biologically active polypeptides and their production from natural or synthetic sources, oligopeptides derived from said polypeptides, and compositions and methods for usefully applying the biological activity associated with the polypeptides and oligopeptides derived therefrom in the health sciences field. More particularly, this invention is directed to a general polypeptide structure which defines proteins having cell growth promoting activity and a novel class of transforming growth factor (TGF) polypeptides which have the property of reversibly conferring the transformed phenotype on normal cells in vitro and thus appear to be proximate effectors of the malignant phenotype. In another particular aspect, this invention is directed to antigenic oligopeptides derived from the TGF polypeptides and to antibodies raised to the antigenic oligopeptides and the associated TGF polypeptides which are useful in the detection and treatment of malignancies. In a further particular aspect, this invention is directed to a class of oligopeptides which have the ability to bind to cellular growth factor receptors and thus to potentially interfere with transformation of certain cell lines into a cancerous state. In a still further particular aspect, this invention is directed to a process for isolating TGF polypeptides in homogeneous form from both transformed human and murine cell lines and body fluids and to the homogeneous TGF polypeptides so obtained. Other particular aspects of this invention are directed to compositions and methods for detection and treatment of cancer and other proliferative diseases and for cell growth associated treatment, for example, wound healing and ulcer treatment. Furthermore, another aspect of this invention is in the treatment and detection of bone-loss diseases, such as osteoporosis and hypercalcemia.

A number of polypeptide hormone and hormone-like growth factors have been found in tissue fluids and their relationship in the control of normal cellular growth or mitosis has been established. These mitogenic polypeptide growth factors include insulin, insulin-like growth factors, platelet-derived growth factor, nerve growth factor. fibroblast growth factor and epidermal growth factor (EGF). At least some of these known growth factors have an effect on the growth of transformed cells, however, on the basis of in vitro tests, it appears that transformed cells require less of these known growth factors for optimal growth and multiplication than do normal cells. In particular, it has been shown, in experiments in cell culture, that the addition of exogenous growth factors such as insulin and EGF can cause normal cells to mimic certain changes in cellular properties that are analogous to transformation; however, they are unable to produce all of the changes associated with the transformed phenotype, e.g., see Sporn et al. (1980) *The New Eng. J. of Med.* 15, pp. 878–880.

Recently, new types of polypeptide growth factors designated as transforming growth factors or TGFs have been found in certain human and animal carcinoma and sarcoma cells which possess a greater complement of the properties apparently essential to phenotypic transformation (Roberts et al. (1980) *Proc. Natl. Acad. Sci. USA* 77, pp. 3494–3498 and Todaro et al. (1980) *Proc. Natl. Acad. Sci. USA* 77, pp. 5258–5262). The TGF polypeptides as a class are characterized by the changes which they cause when applied to untransformed, non-neoplastic indicator cells growing in culture. These changes include (a) loss of density-dependent inhibition of cell growth in monolayer culture, (b) overgrowth of cells in monolayer culture, (c) change in cellular shape, with the result that the indicator cells assume the neoplastic phenotype, and (d) acquisition of anchorage-independence, with the resultant ability to grow in soft agar. The property of anchorage-independent growth of cells in culture has a particularly high correlation with neoplastic growth in vivo. At least certain of the TGF polypeptides show some relationship with EGF in that they are both heat-stable. acid-stable peptides sensitive to reducing agents and proteases and they appear to specifically interact with, and produce biological effects through, cellular membrane EGF receptors. TGF competing with EGF for binding to the cellular EGF receptor. However, TGF is distinguishable from EGF in several important respects. In particular, EGF does not induce anchorage-independent growth of cells in culture nor do antibodies to EGF detect TGF in either radioimmunoassay or immunoprecipitation tests. Further. EGF has only a slight effect on the phenotype of cultured cells, whereas TGF produces a more pronounced phenotypic alteration in cultured cells and confers on them the ability to behave as transformed cells. Interestingly. the transformation produced by TGF is not permanent but reversible in the absence of TGF and there is no evidence that TGF acts as a complete carcinogen itself. (Todaro et al. (1981) *J. of Supramolecular Structure and Cell Biochem.* 15, pp. 287–301).

Thus, TGF polypeptides are a unique class of proteins distinguishable from other growth factors such as EGF from the standpoint of both biological properties and chemical structure. These TGFs. in turn. possess a variety of properties of value or potential value in the health sciences field including potent, but reversible. cell growth or mitogenic properties which find use in cell repair including, for example, wound healing and ulcer therapy. Additionally, the production of TGF polypeptides, or elevated levels of production, are characteristic of, if not essential to, the morphologic transformation of certain cell lines in both human and murine tissue and/or fluids; therefore, the TGF polypeptides or antigenic fragments thereof are of value in differentiating normal cells from tumor cells and antibodies raised thereto have application in both the diagnosis and treatment of malignancies. Further, realization that certain TGF polypeptides specifically interact with and produce their biological effects through cellular membrane EGF receptors raises the possibility, once the basic TGF polypeptide structure is determined, of correlating its structure with the structure of EGF to develop oligopeptides having chemical characteristics to allow binding to the EGF receptors without concomitant phenotypic transformation of the cell. Oligopeptides having this characteristic EGF receptor binding ability find application in treatment of malignancies, since the oligopeptide will interfere or compete with TGF for available receptor sites and thereby interrupt the expression of the transformed properties of the cell.

With the present invention, a method has been developed to obtain TGF polypeptides in sufficient quantity and purity to allow complete structure determination and as a result of this determination and other observations, including the finding of substantial homology between human and murine TGFs, a basic peptide structure has been discovered which has broad application in cell mitosis and the cell growth related field of use. Further, homogeneous TGF polypeptides are obtained having application in both the cell growth field and in the detection and treatment of cancer and other proliferative diseases.

TGF polypeptides, oligopeptides and antibodies raised to these polypeptides also have application in the detection and treatment of bone-loss diseases, such as osteoporosis, hypercalcemia and bone resorption.

Additionally, antigenic oligopeptides and oligopeptides having the ability to bind to cellular growth factor receptors are derived from the basic peptide structure and the determined TGF polypeptide structures. Finally, compositions and methods, including antibodies raised to the TGF polypeptides and antigenic oligopeptides derived therefrom are provided for use in the health sciences field.

2. Description of the Prior Art

Marquardt and Todaro (1982) *J. of Bio. Chem.* Vol. 257, No. 9, pp. 5220–5225, (published May 10, 1982) describe the isolation of a low molecular weight human TGF from serum-free medium conditioned by a human metastatic melanoma tumor line by a sequence of process steps including extraction in 1M acetic acid and sequential purification on reversed phase high pressure liquid chromatography eluting first with acetonitrile solvent followed by elution with 1-propanol to afford a purified TGF having characteristic TGF biological activity, e.g., induction of anchorage-independent cell growth. Twardzik et al. (1982) *Science* 216, pp. 894–897 (published May 21, 1982) report the use of the same purification methodology to purify a TGF from a virus transformed rat cell. The biological activity of the purified materials in the cell culture is also demonstrated. Pike et al. (1982) *J. of Bio. Chem.* Vol. 257, No. 24, pp. 14628–14631 (published Dec. 25, 1982) disclose that both partially purified rat and human TGF have the ability to activate a protein kinase in human tumor cell membranes and therefore to stimulate phosphorylation of a synthetic tyrosine-containing peptide. The only other molecules so far described that have this activity are EGF, insulin and platelet derived growth factor, all of which are believed to have important physiologic functions in man and animal. Other references of interest are cited in the aforementioned articles.

SUMMARY OF THE INVENTION

A basic protein structure has now been found which defines a new class of biologically active molecules. The finding of this framework polypeptide affording biological activity, particularly in the cell growth promotion area, is based on the discovery that a definite correlation exists between the three dimensional structure of certain polypeptides, including TGFs, containing multiple disulfide bonds and the biological activity attributable to the polypeptide. Accordingly, in one of its broadest aspects, the present invention is directed to biologically active polypeptides containing at least one peptide sequence of the formula I:

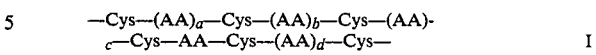

—Cys—(AA)$_a$—Cys—(AA)$_b$—Cys—(AA)$_c$—Cys—AA—Cys—(AA)$_d$—Cys—     I wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8. Also contemplated are compounds according to formula I wherein when b is 4, AA may also be Ile or Met, in addition to the amino acid residues recited above.

Another aspect of the present invention is directed to specific classes of polypeptides having transforming growth factor properties which include compounds of the formulas II and IIA or oligomers thereof:

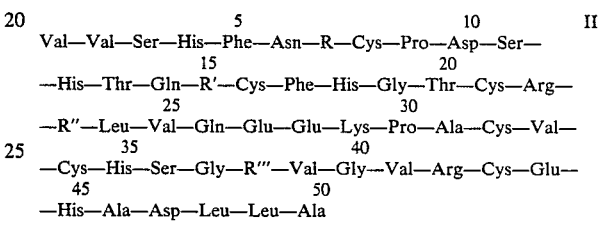

```
                 5                      10              II
Val—Val—Ser—His—Phe—Asn—R—Cys—Pro—Asp—Ser—
             15                      20
—His—Thr—Gln—R'—Cys—Phe—His—Gly—Thr—Cys—Arg—
             25                      30
—R"—Leu—Val—Gln—Glu—Glu—Lys—Pro—Ala—Cys—Val—
             35                      40
—Cys—His—Ser—Gly—R'"—Val—Gly—Val—Arg—Cys—Glu—
             45                      50
—His—Ala—Asp—Leu—Leu—Ala
```

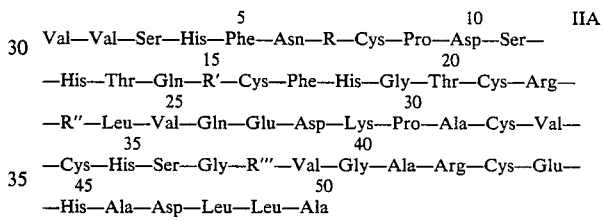

```
                 5                      10              IIA
Val—Val—Ser—His—Phe—Asn—R—Cys—Pro—Asp—Ser—
             15                      20
—His—Thr—Gln—R'—Cys—Phe—His—Gly—Thr—Cys—Arg—
             25                      30
—R"—Leu—Val—Gln—Glu—Asp—Lys—Pro—Ala—Cys—Val—
             35                      40
—Cys—His—Ser—Gly—R'"—Val—Gly—Ala—Arg—Cys—Glu—
             45                      50
—His—Ala—Asp—Leu—Leu—Ala
``` wherein R is Asp or Lys. R' is Phe or Tyr, R" is Ser or Phe, and R'" is Phe or Tyr. Also within the scope of the invention are antigenic oligopeptides derived from the polypeptides of formulas II and IIA.

An additional aspect of this invention relates to polypeptide growth factors containing one or more of the following peptide fragments:

A.   Val-Val-Ser-His-Phe-Asn-Lys-Cys-Pro-Asp-Ser-His-Thr-Gln-Tyr-Cys-Phe-His-Gly-Thr-Cys

B.   Val-Val-Ser-His-Phe-Asn-Asp-Cys-Pro-Asp-Ser-His-Thr-Gln-Phe-Cys-Phe-His-Gly-Thr-Cys

C.   Leu-Val-Gln-Glu-Glu-Lys-Pro-Ala-Cys-Val-Cys-His-Ser-Gly

D.   Cys-His-Ser-Gly-Tyr-Val-Gly-Val-Arg-Cys-Glu-His-Ala-Asp-Leu-Leu-Ala

E.   Leu-Val-Gln-Glu-Asp-Lys-Pro-Ala-Cys-Val-Cys-His-Ser-Gly and

F.   Cys-His-Ser-Gly-Tyr-Val-Gly-Ala-Arg-Cys-Glu-His-Ala-Asp-Leu-Leu-Ala.

A still further aspect of the present invention is directed to a class of oligopeptides which have an ability to bind cellular growth factor receptors. and therefore, have potential utility in treatment of malignancy and other disorders of cell proliferation. This class of oligopeptides is based on the discovery of key sequences in larger polypeptide molecules which exhibit both significant amino acid sequence homology in the appropriate three dimensional structure and have the ability to bind to cellular growth receptor sites. Accordingly, this aspect of the invention provides oligopeptides having the formula III:

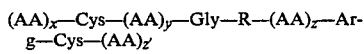

wherein R is Phe or Tyr and AA is an amino acid residue selected from Val, Asn, His, Ser, Ile, Gly, Leu, Asp, Cys, Thr, Ala, Tyr, Pro, Glu, Gln, and Arg, and x is 0 or an integer of from 1 to 6, y is 2, z is 3, and z' is 0 or an integer of from 1 to 6.

Also contemplated by the invention are biologically active compositions and methods using the polypeptide and oligopeptide structures given above including antibodies to the polypeptides of formulas II and IIA and the antigenic oligopeptides derived therefrom, said antibodies being optionally labeled with a label capable of providing a detectable signal for use in diagnostic methods or labeled with a cytotoxic agent for use in cancer or proliferative disease therapy. Other compositions and methods utilizing the cell growth promoting properties of the polypeptides of the present invention also form part of the present invention.

Another aspect of the present invention includes a process for isolating homogeneous transforming growth factor polypeptides from less pure aqueous solutions containing said polypeptides. including body fluids and aqueous mediums conditioned with transforming growth factor-producing cell lines, as well as the homogeneous transforming growth factor polypeptides produced thereby and antibodies raised to said homogeneous polypeptides. In its broadest aspects, the process of the invention involves isolation of a homogeneous transforming growth factor polypeptide from an aqueous medium containing said transforming growth factor polypeptide in impure form by the process steps comprising:

(1) dialyzing the aqueous medium containing the transforming growth factor in impure form against aqueous acetic acid to afford a solvent phase containing transforming growth factor polypeptide which phase is concentrated and optionally clarified, (2) reconstituting the concentrated solvent phase of step (1) with aqueous acetic acid and subjecting the reconstituted solution to gel permeation chromatography by applying reconstituted solution to a gel permeation chromatography column conditioned with aqueous acetic acid and eluting with aqueous acetic acid to obtain selected fractions of eluate containing transforming growth factor polypeptide in an enhanced state of purity, said selected fractions being combined and concentrated, to afford a partially purified, transforming growth factor polypeptide-containing product, (3) subjecting the partially purified, transforming growth factor polypeptide-containing product of step (2) to sequential reverse phase high pressure chromatography by passing said product, after reconstitution in aqueous trifluoroacetic acid, through one or more hydrocarbon bonded silica matrix columns, which have been equilibrated with aqueous trifluoroacetic acid, under high pressure liquid chromatography conditions, the initial column elution being performed using a linear acetonitrile gradient in aqueous trifluoroacetic acid and the subsequent column elution, which is carried out on the combined, transforming growth factor polypeptide-containing fractions of the initial high pressure chromatography step, being performed using a linear 1-propanol gradient in aqueous trifluoroacetic acid, said 1-propanol gradient being increased in sufficiently small 1-propanol concentration increments to afford the transforming growth factor polypeptide as a single distinct peak in the state of a homogeneous polypeptide.

DESCRIPTION OF THE PREFERRED EMBODIMENTS

The peptide sequence which characterizes the basic protein structure according to the invention contains six cysteine residues positioned at critical positions in the polypeptide framework. It is speculated that the positioning of the cysteine residues allows the polypeptide to fold in a particular fashion as a result of disulfide bridges between paired cysteines, and therefore to present a three-dimensional structure which contributes to the biological activity of the resulting protein. There is some evidence suggesting a particular disulfide bridging sequence wherein (numbering the Cys residues (in formula I above) 1 through 6 going from left to right) Cys-1 is bonded to Cys-3, Cys-2 is bonded to Cys-4 and Cys-5 is bonded to Cys-6 by disulfide bonds in biologically active forms of the basic protein structure. The exact chemical nature of the amino acid residues recited for the amino acid sequences spaced between the Cys residues in formula I do not appear to be particularly critical provided at least 10 different amino acids from the group recited for formula I are employed and no amino acid is repeated more than four, preferably three, times as consecutive residues in any given sequence. Of the amino acid residues listed for formula I, preference is given to Val, Ser, His, Phe, Lys, Asp, Thr, Gln, Leu, Glu, Pro, Ala, and Gly. A preferred group of biologically active polypeptides having at least one peptide sequence of formula I are polypeptides and oligomers thereof of the formula IV:

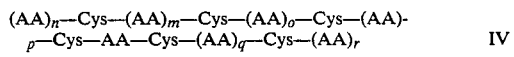

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12. In this preferred group, even further preference is given to polypeptides or oligomers thereof wherein o is 4 and n and r are 7. Within this preferred group, the amino acid residues designated by AA may also be Ile and/or Met, in addition to the amino acid residues recited previously for formula IV. Most preferred are polypeptides wherein the amino acid residues in the sequences spaced between the Cys residues are selected from Val, Ser, His, Phe, Lys, Asp, Thr, Gln, Leu, Glu, Pro, Ala and Gly. Typically the polypeptides in accordance with formulas I and IV will have molecular weights ranging from about 5,000 to about 35,000. Preferred polypeptides in this respect have molecular weights in the range of 5,000 to 8,000.

As noted above, the present invention also contemplates a new class of TGF polypeptides and oligomers thereof of the formulas (formulas II and IIA above):

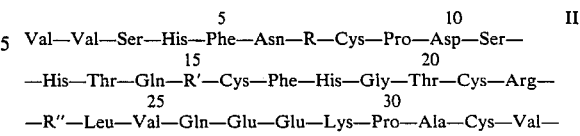

-continued
```
                          35              40
—Cys—His—Ser—Gly—R'''—Val—Gly—Val—Arg—Cys—Glu—
      45                 50
—His—Ala—Asp—Leu—Leu—Ala
```

```
                  5                  10             IIA
Val—Val—Ser—His—Phe—Asn—R—Cys—Pro—Asp—Ser—
                     15                 20
—His—Thr—Gln—R'—Cys—Phe—His—Gly—Thr—Cys—Arg—
                       25             30
—R"—Leu—Val—Gln—Glu—Asp—Lys—Pro—Ala—Cys—Val—
                          35              40
—Cys—His—Ser—Gly—R'''—Val—Gly—Ala—Arg—Cys—Glu—
      45                 50
—His—Ala—Asp—Leu—Leu—Ala
``` wherein R is Asp or Lys, R' is Phe or Tyr, R" is Ser or Phe, and R''' is Phe or Tyr. This novel class of polypeptides is derived from the finding that certain TGFs obtained from a variety of mammalian species (both murine and human) have substantial homology in the amino acid make-up of the peptide sequence (greater than 90% of the sequences being identical) as well as substantially the same biological properties. In particular, TGF polypeptides in accordance with the formulas given above cause the loss of density-dependent inhibition of cell growth in monolayer culture, overgrowth in monolayer culture, characteristic change in cellular morphology and acquisition of anchorage-independent growth when applied to untransformed, non-neoplastic, indicator cells grown in culture. In addition to being extremely potent cell growth promoters and effectors of cell transformation, the TGF polypeptides in accordance with the above formulas compete with EGF for binding to the cellular EGF receptor and also have the ability to activate an enzyme, a protein kinase, in human tumor cell membranes. Preferred TGF polypeptides of formula II above include those wherein R is Asp. R' is Phe, R" is Ser, and R''' is Phe, or where R is Lys, R' is Tyr, R" is Phe, and R''' is Tyr. Preferred TGF polypeptides of formula IIA above include those wherein R is Asp, R' is Phe, R" is Phe, and R''' is Tyr. As will be discussed in greater detail below, these TGF polypeptides may be suitably obtained from a variety of transformed human and murine cell lines, certain embryonic cell lines and body fluids of tumor-carrying mammals using the isolation process of the invention or by conventional synthetic or recombinant means for synthesizing polypeptides. Typically the molecular weight of the TGF polypeptides and oligomers thereof of formulas II and IIA will be in the range of from about 5,000 to about 35,000. In this regard, preference is given to TGF polypeptides having a molecular weight of about 5,000 to 8,000.

Recognition of the substantial peptide sequence homology in the novel class of TGF polypeptides of formulas II and IIA above and the commonality of biological properties associated therewith allows for further definition of a class of polypeptide growth factors which are within the scope of the present invention. These polypeptide growth factors are defined as containing one or more of the following peptide fragments:

A. Val-Val-Ser-His-Phe-Asn-Lys-Cys-Pro-Asp-Ser-His-Thr-Gln-Tyr-Cys-Phe-His-Gly-Thr-Cys

B. Val-Val-Ser-His-Phe-Asn-Asp-Cys-Pro-Asp-Ser-His-Thr-Gln-Phe-Cys-Phe-His-Gly-Thr-Cys

C. Leu-Val-Gln-Glu-Glu-Lys-Pro-Ala-Cys-Val-Cys-His-Ser-Gly, and

D. Cys-His-Ser-Gly-Tyr-Val-Gly-Val-Arg-Cys-Glu-His-Ala-Asp-Leu-Leu-Ala

E. Leu-Val-Gln-Glu-Asp-Lys-Pro-Ala-Cys-Val-Cys-His-Ser-Gly, and

F. Cys-His-Ser-Gly-Tyr-Val-Gly-Ala-Arg-Cys-Glu-His-Ala-Asp-Leu-Leu-Ala.

Preferred polypeptides in this respect. include polypeptides containing a combination of peptide fragments A and C or B and E and polypeptides containing a combination of peptide fragments B and C. Most preferred are polypeptides containing fragments B, C and D or B and E. Here again, the polypeptide growth factors containing one or more of peptide fragments A, B, C, D, E, and F will generally have molecular weight in the range of from about 7,000 to about 35,000, preferably from 1,000 to 8,000. The lower end of the molecular weight range would include the above specified peptide fragments themselves as complete polypeptides having the characteristic growth factor biological activity.

Previously it has been noted that the TGF polypeptides of the present invention are of value in the detection of malignancies in mammals, since the production and/or elevated levels of production of the TGF polypeptides are characteristic of morphologic transformation of certain human and murine cell lines. In this regard, antibodies to the TGF polypeptides have utility in diagnosis of malignancy, since they can be used to detect extremely low levels of TGF polypeptide present in tumor cells or in body fluids. While the entire TGF polypeptide molecule can be used to generate antibodies (both polyclonal and monoclonal), it is also possible, and advantageous from the standpoints of cost and technical effort, to determine various regions in the TGF polypeptide sequence which are likely to be determinant sites and to use these oligopeptides of at least about eight amino acids, typically at least about 10 and not more than about 20 amino acids, to define a hapten which can be used to induce antibody formation. As further discussed below, the oligopeptide is bound to an appropriate immunogen and introduced into a vertebrate to produce the desired antibodies. Accordingly, the present invention also provides a series of oligopeptides corresponding to antigenic regions in the TGF polypeptides. Exemplary species of the antigenic oligopeptides useful in generating antibodies in accordance with the present invention are listed below:

A. Val-Val-Ser-His-Phe-Asn-Asp-Cys-Pro-Asp-His-Thr

B. Val-Val-Ser-His-Phe-Asn-Lys-Cys-Pro-Asp-His-Thr

C. Arg-Phe-Leu-Val-Gln-Glu-Glu-Lys-Pro-Ala

D. Arg-Tyr-Leu-Val-Gln-Glu-Glu-Lys-Pro-Ala

E. Cys-His-Ser-Gly-Phe-Val-Gly-Val-Arg-Cys-Glu-His-Ala-Asp-Leu-Leu-Ala

F. Cys-His-Ser-Gly-Tyr-Val-Gly-Val-Arg-Cys-Glu-His-Ala-Asp-Leu-Leu-Ala

G. Arg-Phe-Leu-Val-Gln-Glu-Asp-Lys-Pro-Ala

H. Arg-Tyr-Leu-Val-Gln-Glu-Asp-Lys-Pro-Ala

I. Cys-His-Ser-Gly-Phe-Val-Gly-Ala-Arg-Cys-Glu-His-Ala-Asp-Leu-Leu-Ala

J. Cys-His-Ser-Gly-Tyr-Val-Gly-Ala-Arg-Cys-Glu-His-Ala-Asp-Leu-Leu-Ala

K. Val-Val-Ser-His-Phe-Asn-Asp-Cys-Pro-Asp-Ser-His-Thr and

L. Val-Val-Ser-His-Phe-Asn-Lys-Cys-Pro-Asp-Ser-His-Thr.

Another compositional aspect of the present invention is directed to a class of oligopeptides which have therapeutic value in treatment of malignancies. These oligopeptides have the ability to bind to cellular growth factor receptors without causing phenotypic transformation of the cell and therefore they can effectively compete with TGF polypeptides for available receptor sites on the cell and interrupt or minimize cell transformation which is characteristic of TGF binding to cell receptors. The oligopeptides according to the invention which have the ability to bind to cellular receptors are of the formula (formula III above):

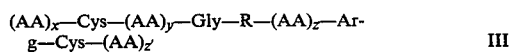

wherein R is Phe or Tyr and AA is an amino acid residue selected from Val, Asn, His, Ser, Ile, Gly, Leu, Asp, Cys, Thr, Ala, Tyr, Pro, Glu, Gln, and Arg, and x is 0 or an integer of from 1 to 6, y is 2, z is 3 and z' is 0 or an integer of from 1 to 6. Preferred oligopeptides in accordance with the above formula include those wherein x and z' are 0 and AA is an amino acid residue selected from Val, His, Ser, Ile, Gly and Asp. A desirable group of biologically active oligopeptides related to those of formula III are those containing two glycine residues in addition to afford a sequence of the following formula:

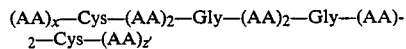

wherein the amino acid residues designated by the AAs are the same as those mentioned for formula III above but include Phe and subscripts x and z' are as given for formula III above. These oligopeptides assume a common three-dimensional structure attributable to the disulfide bridging between the two cysteines. This disulfide bridge characterizes the biologically active forms of the oligopeptides. Particularly preferred oligopeptides in this regard are selected from the class consisting of:

(1) Cys-His-Ser-Gly-Tyr-Val-Gly-Val-Arg-Cys
(2) Cys-His-Ser-Gly-Phe-Val-Gly-Val-Arg-Cys
(3) Cys-His-Ser-Gly-Tyr-Val-Gly-Ala-Arg-Cys
(4) Cys-His-Ser-Gly-Phe-Val-Gly-Ala-Arg-Cys and
(5) Cys-Ser-His-Gly-Tyr-Thr-Gly-Ile-Arg-Cys.

The polypeptides and oligopeptides according to the invention as defined by the structural formulas (formulas I through IV) and peptide sequences given above can be prepared by synthetic techniques, techniques whereby the peptide is isolated from a naturally occurring source, e.g., cell lines and body fluids, and by techniques employing hybrid DNA technology. For those polypeptides and oligopeptides of the invention containing up to about 50 amino acid residues, conventional solid phase peptide synthesis is suitably employed. In this general synthetic procedure for making peptides, which is described, for example, in U.S. Pat. No. 4,341,761 to Ganfield et al., employs known side-chain protecting groups and conventional polystyrene resins supports—e.g., chloromethylated resins, hydroxymethyl resins or benzhydrylamine resins—to affect the amino acid coupling. For polypeptides containing in excess of about 50 amino acid residues, the process according to the invention for isolating homogeneous TGFs from natural sources (which is described in detail below) can be suitably employed to obtain pure forms of the desired peptide. In this regard, particularly suitable sources of the TGF polypeptides according to the invention include serum-free medium conditioned by retrovirus-transformed Fischer rat embryo fibroblasts, in particular fibroblasts transformed with Snyder-Theilen feline sarcoma virus, Moloney murine sarcoma virus-transformed mouse 3T3 cells and human metastatic melanoma cell lines A2058 and A375. Sources and methods for suitable murine cell lines are described in DeLarco et al. (1980) *J. Biol. Chem.* 255, pp. 3685–3690 and Ozanne et al. (1980) *J. Cell. Physiol.* 105, pp. 163–180. Sources and methods for human cell lines are similarly described in Todaro et al. (1980) *Proc. Natl. Acad. Sci. USA* 77, pp. 5258–5262 and Giard et al. (1973) *J. Natl. Cancer Inst.* 51, pp. 1417–1423. The isolation process of the invention described below can also be used to obtain TGF polypeptides according to the invention from various body fluids such as urine, serum, plasma, whole blood or cerebrospinal fluid of human or murine subjects carrying malignancies or transformed cells which produce TGF polypeptides. In this regard, a suitable source of TGF polypeptides according to the invention is the urine or other body fluids of mice which have been inoculated with tumor cells (human melanoma or transformed rat) known to produce TGF polypeptides. In all cases the identification and purity of the TGF polypeptide can be monitored by a radioreceptor assay based on receptor cross-reactivity with EGF (see experimental examples below). In techniques utilizing recombinant or hybrid DNA technology, the oligopeptides according to the invention or segments of the polypeptides according to the invention containing up to, for example, 20 amino acids can be used to deduce the codon sequence for single stranded nucleotide (DNA) probes. These nucleotide probes can then be synthesized using known synthetic techniques and used as a probe to obtain messenger RNA (mRNA) coding for growth factor-type polypeptides in both normal and transformed cells or body fluids containing said peptides. Once messenger RNA is obtained, conventional techniques can be used for reverse transcribing of the mRNA to complementary DNA (cDNA) and subsequent cloning of the cDNA in a suitable vector to obtain expression of the desired polypeptide.

The process according to the invention provides a uniquely effective means of obtaining TGF polypeptides in homogeneous form from various aqueous based fluids containing less pure forms of the TGF polypeptides such as serum-free mediums conditioned by transformed cell lines which produce TGF polypeptides or body fluids, e.g., urine, from mammals carrying malignancies or transformed cells which produce the TGF polypeptides. Important aspects of this unique isolation or purification process include an initial extraction or dialysis step using aqueous acetic acid, subsequent gel permeation chromatography of the acid-soluble TGF-containing activity, and finally, reverse phase high pressure liquid chromatography using sequentially acetonitrile and 1-propanol in the presence of aqueous trifluoroacetic acid. Broadly defined, this process involves isolation of a homogeneous transforming growth factor polypeptide from an aqueous medium containing said transforming growth factor polypeptide in impure form by the process steps comprising:

(1) dialyzing the aqueous medium containing the transforming growth factor in impure form against aqueous acetic acid to afford a solvent phase containing transforming growth factor polypeptide which phase is concentrated and optionally clarified, (2) reconstituting the concentrated solvent phase of step (1) with aqueous acetic acid and subjecting the reconstituted solution to gel permeation chromatography by applying reconstituted solution to gel permeation chromatography column conditioned with aqueous acetic acid and eluting with aqueous acetic acid to obtain selected fractions of eluate containing transforming growth factor polypeptide in an enhanced state of purity, said selected fractions being combined and concentrated, to afford a partially purified, transforming growth factor polypeptide-containing product, (3) subjecting the partially purified, transforming growth factor polypeptide-containing product of step (2) to sequential reverse phase high pressure chromatography by passing said product, after reconstitution in aqueous trifluoroacetic acid, through one or more hydrocarbon bonded silica matrix columns, which have been equilibrated with aqueous trifluoroacetic acid, under high pressure liquid chromatography conditions, the initial column elution being performed using a linear acetonitrile gradient in aqueous trifluoroacetic acid and the subsequent column elution, which is carried out on the combined, transforming growth factor polypeptide-containing fractions of the initial high pressure chromatography step, being performed using a linear 1-propanol gradient in aqueous trifluoroacetic acid, said 1-propanol gradient being increased in sufficiently small 1-propanol concentration increments to afford the transforming growth factor polypeptide as a single distinct peak in the state of a homogeneous polypeptide.

In a preferred application, the process according to the invention is employed to isolate homogeneous TGFs from serum-free media conditioned by transformed, TGF-producing cell lines. In this preferred application, the conditioned medium is suitably clarified. e.g., by centrifugation. and concentrated prior to dialysis and the TGF-containing solvent phase from dialysis is suitably clarified, e.g., by centrifugation, as well as concentrated prior to gel permeation chromatography. In any case, the dialysis is suitably carried out using an aqueous acetic acid solvent having an acetic acid concentration of from 0.01 to 1 molar, with 0.1 molar acetic acid being preferred. The gel permeation chromatography may be carried out using a variety of gels conventionally employed to separate proteins or polypeptides based on molecular size. Suitable gels include dextran gels, agarose gels and polyacrylamide gels. In this regard, preference is given to polyacrylamide gel filtration resins (Bio-Gels ) such as Bio-Gel P-10, Bio-Gel P-30 and Bio-Gel P-60, Bio-Gel P-10 being especially preferred. The aqueous acetic acid used to condition the column and to elute the TGF-containing fractions suitably has an acetic acid concentration of from 0.2 to 2.0 molar, with 1.0 molar acetic acid being preferred. The TGF-containing fractions which elute from the column can be identified by determining their EGF-competing activity and growth promotion activity in soft agar (see experimental examples below). After gel permeation chromatography, the fractions containing TGF polypeptides in an enhanced state of purity are pooled together and concentrated for example, by lyophilization as a preparation step for further purification by reverse phase high pressure liquid chromatography (HPLC).

The final stage of the purification process of the invention involves sequential HPLC with acetonitrile and 1-propanol in the presence of aqueous trifluoroacetic acid. This sequential HPLC can be carried out using one or more HPLC columns, but it is preferred to carry out the sequential HPLC steps using a single HPLC column. The column packing employed is suitably a porous silica matrix to which a long chain hydrocarbon, for example. hydrocarbon containing 16 to 22 carbon atoms, is bound. Preferred packings are $\mu$Bondapak hydrocarbon columns, in particular $\mu$Bondapak $C_{18}$ column (10-$\mu$m particle size, 0.39 × 30 cm, Waters Associates). Typically, the procedure is carried out under pressure. preferably in the range of from about 50 to 5,000 pounds per square inch (psi). Prior to application to the column, the concentrated TGF-containing fractions are reconstituted in an aqueous 1 to 10% trifluoroacetic acid and adjusted to a pH in the range of 2 to 5, preferably 3.5 by the addition of trifluoroacetic acid. The column is suitably equilibrated with 0.01 to 0.1% aqueous trifluoroacetic acid, preferably 0.05% aqueous trifluoroacetic acid, before sample injection. The first elution is carried out with acetonitrile in a 0.01 to 0.1%, preferably 0.05% trifluoroacetic acid, using a linear acetonitrile gradient (acetonitrile concentration increased linearly at a gradient in the range of about 0.1%/min to about 1%/min). The elution is carried out over a time period of from 0.2 to 3 hours at a flow rate of about 0.2 to 2 ml/min and at a temperature of from 10° to 50° C., preferably about 40° C. The pooled fractions containing TGF activity as determined by EGF competition and soft agar assay are concentrated, for example, by lyophilization, prior to the second step of the HPLC using 1-propanol solvent. For the second step of the sequential HPLC, the pooled and concentrated fractions from the first HPLC elution are reconstituted in 0.01 to 0.1% trifluoroacetic acid and rechromatographed on the same column or a second column equilibrated with trifluoroacetic acid in a manner identical to that used for the first column. This second elution is carried out with 1-propanol in a 0.01 to 0.1%, preferably 0.035% trifluoroacetic acid using a linear 1-propanol gradient. It is important for optimum results to employ a shallow linear 1-propanol gradient in this step. In particular, the 1-propanol concentration should be increased linearly at a gradient which does not exceed 0.1%/min and preferably the linear 1-propanol gradient should be maintained between 0.01%/min and 0.05%/min during the elution. This second elution is suitably carried out over a time period of from 1 to 5 hours at a flow rate of about 0.5 to 5 ml/min and at a temperature of from 10° to 60° C., preferably about 40° C. By controlling the linear 1-propanol concentration gradient at the shallow levels given above, it is possible to elute TGF polypeptides as well-defined peaks of TGF activity in the form of homogeneous polypeptides.

With the isolation process of the invention, it is possible to recover up to about 70% of the initial TGF activity in the impure starting material while achieving degrees of purification in excess of 200,000-fold. The homogeneous TGF polypeptides obtained by the isolation process of the invention typically have molecular weights in the range of about 5,000 to about 35,000 and are of sufficient purity to permit peptide sequencing. Preferred homogeneous TGF polypeptides, which are obtained with the process of the invention, include TGFs having apparent molecular weights of 7,400, 20,000 and 30,000 to 35,000. These homogeneous TGF polypeptides show characteristic biological properties of TGF polypeptides when they are applied to untransformed, non-neoplastic indicator cells growing in culture, including acquisition of anchorage-independence, with the resultant ability to grow in soft agar. Further, the homogeneous TGF polypeptides can be used to raise antibodies (see below) which have value in the detection and treatment of cancer and other proliferative diseases in accordance with the invention. In this regard, it is not essential that each of the forms of the TGF be purified to homogeneity in order to produce antibodies to the different TGF peptides. These various forms of antibodies to the TGF polypeptides are also contemplated by this invention.

Antibodies according to the invention include both monoclonal and polyclonal antibodies raised to the TGF polypeptides of formulas II and IIA given above, antigenic oligopeptides derived from the TGF polypeptides of formulas II and IIA and the homogeneous TGF polypeptides obtained using the isolation process of the invention from various transformed cell lines and body fluids of mammals carrying malignancies or transformed cells. The antibodies according to the invention can be prepared in a variety of ways known in the art, depending on whether monoclonal or polyclonal antibodies are desired. For polyclonal antibodies, a vertebrate, typically a domestic animal, is hyperimmunized with antigen and the blood collected shortly after repeat immunizations and the gamma globulin isolated. Suitable methods for preparing polyclonal antibodies are described in the *Handbook of Experimental Immunology*, 3rd edition. Weir, Editor, Blackwell Scientific publications, Oxford and London, 1978. For monoclonal antibodies, a small animal, typically a mouse or rat, is hyperimmunized with antigen, the spleen removed and the lymphocytes fused with myeloma cells in the presence of a suitable fusion promoter. The resulting hybrid cells or hybridomas are screened to isolate individual clones, each of which secrete a single antibody species to the antigen. The individual antibody species obtained in this way are each the product of a single B cell from the immune animal generated in response to a specific antigenic site recognized on the immunogenic substance. The general process for obtaining monoclonal antibodies, including those according to the invention, is described by Kohler and Milstein (1975) *Nature* 256, pp. 495–497. The polypeptides and antigenic oligopeptides of the invention used to produce antibodies (both polyclonal and monoclonal) may be employed directly in the immunization procedure or they may be bound to a suitable carrier-protein using methods known in the art, for example, see U.S. Pat. No. 4,341,761 to Ganfield et al. Use of a carrier protein is particularly preferred when the immunization is carried out using the antigenic oligopeptides of the invention.

The antibodies according to the invention may be used in a variety of ways. In a preferred application, they may be used for diagnosis of malignancy and other proliferative diseases. In instances where the antigen may be found in a physiological fluid or at a concentration differential only when malignancy or other proliferative disease exists, the physiological fluid. such as serum. plasma, whole blood or cerebrospinal fluid may be assayed. Antibodies employed in assays may be labeled or unlabeled. Unlabeled antibodies may be employed in agglutination; labeled antibodies may be employed in a wide variety of assays, employing a wide variety of labels, such as radionuclides, enzymes, fluorescers, enzyme substrates or cofactors, or the like. These techniques are amply defined in the literature and exemplary assays may be found in U.S. Pat. Nos. 3,817,834, 3,935,074, 4,233,402 and 4,318,980, as illustrative.

In some techniques it will be useful to label the antigen or fragment thereof, rather than the antibody, and have a competition between labeled antigen and antigen in the sample for antibody. In this situation, it is common to provide kits which have the combination of the labeled antigen or labeled fragment and the antibody in amounts which provide for optimum sensitivity and accuracy. In other situations, it is desirable to have a solid support, where either antigen or antibody is bound. A polyepitopic antigen can serve as a bridge between antibody bound to a support and labeled antibody in the assay medium. Alternatively. one may have a competition between labeled antigen and any antigen in the sample for a limited amount of antibody.

Where the antigen may not be found in a physiological fluid or if found there is not diagnostic of malignancy or the target proliferative disease, then cells will have to be isolated and the cells assayed for the presence of the antigen. For detecting the antigen, the tissue sample may be lysed by conventional methods, e.g., base, detergents, or the like, cellular debris separated by filtration or centrifugation and the filtrate or supernatant isolated and assayed.

For purposes of therapy, either xenogeneic or allogeneic antibodies may be employed, depending upon the nature of the treatment, and whether the foreign antibodies will induce an immune response. The literature has described a number of ways of making human antibodies, where it is found that mouse or other mammalian antibodies are not satisfactory. The antibodies may be used in a wide variety of ways. By employing the appropriate IgG (other than IgG$_1$), one may induce lysis through the natural complement process. Alternatively, the lysing portion of a toxin may be joined to the antibodies, particularly a Fab fragment. The antibodies may be bound to liposomes for directing the liposomes to the malignant cells to become ingested by the cells by merging of the membranes. Other labels may also be bound to the antibodies, such as radionuclides, fluorescers, enzymes, and the like. By introducing the antibodies in vivo, the antibodies will direct the label to the malignant cell, where the presence of malignancy may be diagnosed or treated.

The formulation of the antibodies will vary widely, depending on the nature of the label, the purpose of the antibodies, the site to which the antibodies are to be directed, and the like. Usually, the antibodies will be formulated in a physiologically acceptable carrier, e.g., saline or phosphate buffered saline, and injected into the host, when possible at the desired site, and when this is not possible, into a circulating system, such as blood.

The antibodies obtained in accordance with this invention can also be used to isolate cells expressing the TGF polypeptides and to remove cells in vitro from a heterogeneous cell population containing cells expressing a TGF polypeptide. Separation can be achieved with a fluorescence activated cell sorter (FACS). This same technique can be used for identifying and isolating cells expressing a TGF polypeptide. For removing cells expressing a TGF polypeptide from a mixture of cells, the subject antibodies may be combined with complement, joined to the lysing fragment (A fragment) of a toxin (see E.P.O. Application No. 17,507 and U.S. patent application No. 2,034,324) or the cells agglutinated and separated by physical means.

Methods and compositions employing the biologically active polypeptides and oligopeptides of the invention are also afforded for treatment of cancer and other proliferative diseases and for therapies wherein cell growth promotion is beneficial. In particular, compositions are provided employing the oligopeptides of formula III above for the treatment of malignancies. Further compositions containing biologically active polypeptides of formulas I, II, and II A for treatment of cancer and other proliferative diseases and for cell growth promotion applications, e.g., wound healing and ulcer therapy are also provided. These therapeutic compositions comprise effective amounts of the indicated oligopeptides and polypeptides in admixture with pharmaceutically acceptable carriers. In particular. pharmaceutical compositions that contain the oligopeptides and/or polypeptides of the invention as an active ingredient will normally be formulated with an appropriate solid or liquid carrier depending upon the particular mode of administration being used. For instance, parenteral formulations are usually injectable fluids that use pharmaceutically and physiologically acceptable fluids such as physiological saline. balanced salt solutions, or the like as a vehicle. Oral formulations, on the other hand. may be solid, e.g., tablet or capsule, or liquid solutions or suspensions.

In the therapeutic methods of the invention, the oligopeptides and/or polypeptides may be administered to humans in various manners such as orally, intravenously, intramuscularly, intraperitoneally. intranasally, intradermally, and subcutaneously. The particular mode of administration and dosage regimen will be selected by the attending physician taking into account the particulars of the patient, the nature of treatment required, and/or the disease state involved. For instance, damaged tissue from wounds is usually treated by daily or twice daily doses over a few days to a few weeks; whereas tumor or cancer treatment involves daily or multidaily doses over months or years. The oligopeptide and/or polypeptide therapy of the invention may be combined with other treatments and may be combined with or used in association with other chemotherapeutic or chemopreventive agents for providing therapy against proliferative diseases, neoplasms. or other conditions against which they are effective.

TGF oligopeptides, polypeptides and antibodies raised to these peptides also are effective in the detection and treatment of bone-loss diseases. For example, TGF activity is present in the material responsible for bone-resorbing activity in tumors associated with hypercalcemia (Ibbotson et al. (1983) *Science* 221, 1292). Increased bone resorption may be an endocrine effect of TGFs secreted by tumor cells.

In addition, elevated levels of TGF stimulate bone resorption through calcium leaching, which is associated with diseases, such as osteoporosis. Osteoporosis is a disease commonly seen in elderly individuals, causing bone loss. The use of antibodies to TGF may be indicative of the existence of osteoporosis. Therefore, TGF antibodies are useful in the analysis and therapy of this important disease.

This invention provides a method for detecting bone loss in a human host which comprises contacting cells or body fluids with an antibody of TGF and determining the level of binding of said antibody to said cells or cellular products in the body as diagnostic of a host with bone loss. Also provided are compositions for treatment of bone-loss disease, employing effective amounts of the oligopeptides. polypeptides, or antibodies of TGF together with a pharmaceutically acceptable carrier therefor.

The following examples are offered by way of illustration and not by way of limitation:

EXAMPLE I

Production, Purification and Characterization of Low Molecular Weight Human Transforming Growth Factors (hTGFs)

A. Experimental Procedures

Source of hTGFs hTGFs were purified from the serum-free medium conditioned by a human metastatic melanoma line A2058 (Todaro et al. (1980) *Proc. Natl. Acad. Sci. USA* 77, pp. 5258–5262) derived from a brain metastasis in a 43-year-old man. Cells were grown to 90% confluency in roller bottles containing Dulbecco's modified Eagle's medium (Grand Island Biological Co., 430–2100), supplemented with 10% calf serum (Colorado Serum Co.,) at 37° C. The cells were washed for 1 h with 50 ml of serum-free Waymouth's medium (Grand Island Biological Co., MD 705/1). This and a second collection of supernatant fluid, 24 h later, were discarded. Subsequent collections were made every other day, or every 3rd day, for a 2-week period.

The medium was collected by decantation. stored for up to 24 h at 4° C. in the presence of the protease inhibitor phenylmethanesulfonyl fluoride (1 $\mu$g/ml), and clarified by continuous flow centrifugation at 32,000 rpm at 4° C. Flow rates of 5 liters/h in the CF-32 continuous flow rotor (Beckman) in the model L5-50 ultracentrifuge (Beckman) were used. The supernatant, after high speed centrifugation, will be referred to as A2058-conditioned medium.

The A2058-conditioned medium was immediately concentrated in the hollow fiber Dialyzer/Concentrator (model DC10, type H10P5-20 cartridge, Amicon Corp.) at 10° C. The concentrate was drained after a 150-fold reduction in volume. The cartridge was washed with 1000 ml of Waymouth's medium. The ultrafiltrate was discarded.

Purification of hTGFs

Dialysis and Centrifugation

The combined retentate and cartridge wash after ultrafiltration of A2058-conditioned medium was dialyzed for 60 h against 0.1M acetic acid in Spectrapor 3 dialysis tubing (Spectrum Medical Industries). The retentate was centrifuged at 100,000×g for 1 h at 4° C. The pellet was discarded. The supernatant was concentrated by lyophilization and reconstituted in 0.5 ml of 1M acetic acid/liter of original A2058-conditioned medium.

Chromatography on Bio-Gel P-10

Following concentration, dialysis, and centrifugation, the supernatant containing hTGF activity was further purified by gel permeation chromatography on a column (2.5×85 cm) (420 ml bed volume) of Bio-Gel P-10 (200–400 mesh, Bio-Rad Laboratories). The column was equilibrated with 1M acetic acid at 22° C. Samples of protein (65–115 mg) in 1M acetic acid (5 ml)

were applied to the column. To ensure a constant flow rate, the column effluent was regulated at 12 ml/h with a peristaltic pump. 4.8-ml fractions were collected. Aliquots were lyophilized for subsequent determinations of EGF-competing activity and growth-promoting activity in soft agar. Fractions representing the major portions of a given peak were pooled and concentrated by lyophilization.

Reverse Phase High Pressure Liquid Chromatography

The final purification of hTGF was achieved by reverse phase HPLC, using the general procedure described in Marquardt et al. (1980) *J. of Biol. Chem.* 256, pp. 6859–6865. All separations were performed on a $\mu$Bondapak $C_{18}$ column (10-$\mu$m particle size, 0.39×30 cm. Waters Associates) at a flow rate of 1 ml/min at 40° C. Lyophilized samples were reconstituted in 0.05% (v/v) trifluoroacetic acid in water, adjusted to pH 2 with 10% (v/v) trifluoroacetic acid, and applied through the sample injector to the column which was equilibrated with 0.05% trifluoroacetic acid. The column was then eluted with a linear acetonitrile gradient in 0.045% trifluoroacetic acid. The column effluent was collected in 1.5-ml fractions. Aliquots were lyophilized for subsequent EGF competition and growth stimulation assays. Pools of fractions comprising the major hTGFs activity were concentrated by lyophilization.

hTGFs-containing pools were reconstituted in 0.05% trifluoroacetic acid and rechromatographed on the same column, previously equilibrated with 0.05% trifluoroacetic acid in water. The column was then eluted with a linear 1-propanol gradient in 0.035% trifluoroacetic acid. The column effluent was collected in 1.5-ml fractions. Aliquots were lyophilized for EGF competition and growth stimulation assays.

SDS-Polyacrylamide Gel Electrophoresis

Sodium dodecyl sulfate (SDS) -polyacrylamide gel electrophoresis was performed as described in Laemmli (1980) *Nature (Lond)* 227, pp. 680–685. A 15–30% acrylamide gradient slab (140×120×0.75 mm) was prepared with a 4% stacking gel. The gels were run at 30 V with an electrode buffer containing Tris (0.05M), glycine (0.38M), and SDS (0.1%, w/v) until the tracking dye (bromphenol blue) had run off the end of the gel. After electrophoresis, gels were fixed in 50% methanol, 10% acetic acid for 2 h, washed in 5% methanol, 7% acetic acid overnight, and stained with silver (Oakley et al. (1980) *Anal. Biochem.* 105, pp. 361–363).

Protein Determination

Total protein was determined using bovine serum albumin as a standard. Prior to protein determination, the starting material was dialyzed against phosphate-buffered saline to remove components of the culture medium interfering with the color reaction or lyophilized, if samples had been dissolved in volatile acids. Protein was also determined by amino acid analysis. Lyophilized samples were hydrolyzed at 110° C. for 24 h in evacuated Pyrex tubes with 0.1 ml of 6N HCl containing 0.1% liquid phenol, and analyzed with a Durrum D-500 analyzer equipped with a PDP 8/A computing integrator using o-phthalaldehyde for the fluorogenic detection of primary amines (Bensen et al. (1975) *Proc. Natl. Acad. Sci. USA* 72, pp. 619–622).

Radioreceptor Assay

Purified EGF was labeled with $Na^{125}I$ by a modification of the chloramine-T method as described in DeLarco et al. (1978) *Proc. Natl. Acad. Sci. USA* 75, pp. 4001–4005. The $^{125}I$-EGF binding assay was performed on subconfluent monolayers of formalin-fixed A431 human carcinoma cells as previously described (in DeLarco et al. (1980) *J. of Biol. Chem.* 255, pp. 3685–3690). The fixed cells were washed twice with 0.5 ml of binding buffer (Dulbecco's modified Eagle's medium containing 1 mg/ml of bovine serum albumin and 50 mM 2-[bis(2-hydroxyethyl)amino]ethanesulfonic acid, pH 6.8). Competitions were initiated by the addition of 0.2 ml of binding buffer containing 0.4 ng of $^{125}I$-EGF with or without potential inhibitor. After incubation for 1 h at 22° C., the specifically bound $^{125}I$-EGF was determined. The TGF content was expressed by its degree of inhibition of the binding of $^{125}I$-EGF to the EGF receptor. One EGF-competing activity unit is defined as the amount of protein that inhibits the binding of $^{125}I$-EGF to its receptor by 50%.

Soft Agar Growth Assay

The assay for colony growth in soft agar, using normal rat kidney fibroblasts, clone 49F, was performed as reported in Todaro et al. (1980) *Proc. Natl. Acad. Sci. USA* 77, pp. 5258–5262. Lyophilized samples to be tested were reconstituted in 0.5 ml of Dulbecco's modified Eagle's medium, supplemented with 10% calf serum. 1.5 ml of 0.5% (w/v) agar (Difco) in the supplemented medium and 0.5 ml of supplemented medium containing $2.3 \times 10^4$ cells were added. 2.3 ml of the resultant mixture were pipetted on a 2-ml base layer (0–5% agar in supplemented medium) in 60-mm Petri dishes (Falcon). The cells were incubated at 37° C. in a humidified 5% $CO_2$/95% air atmosphere. The assay was read unfixed and unstained at 5 days and at 10–14 days.

B. Results

Source, Concentration, and Initial Fractionation of hTGFs hTGFs was isolated from serum-free conditioned medium of the highly transformed human metastatic melanoma cell line, A2058. The quantitation of hTGFs was based on two of its properties: the capacity to induce anchorage-independent growth of normal rat kidney fibroblasts in soft agar, and the ability to compete with $^{125}I$-EGF for the EGF receptor sites on A431 human carcinoma cells. A summary of the steps leading to the isolation of hTGFs and its recovery is presented in Table I.

TABLE I

| | Purification of hTGFs from conditioned medium of human melanoma cells, A2058 | | | | |
|---|---|---|---|---|---|
| Purification step | Protein[a] recovered mg | EGF-competing activity recovered units[b] | Relative specific activity units/mg | Degree of purification -fold | Recovery % |
| 1. A2058-conditioned medium | 1,020 | 4,525 | 4.4 | 1 | 100 |
| 2. Acid-soluble supernatant | 837 | 4,299 | 5.1 | 1 | 95 |

TABLE I-continued

| | Purification of hTGFs from conditioned medium of human melanoma cells, A2058 | | | | |
|---|---|---|---|---|---|
| Purification step | Protein[a] recovered mg | EGF-competing activity recovered units[b] | Relative specific activity units/mg | Degree of purification -fold | Recovery % |
| 3. Bio-Gel P-10 | | | | | |
|    Pool P-10-A | 29.7 | 2,077 | 70 | 16 (1) | 45.9 (100) |
|    Pool P-10-B | 14.5 | 2,033 | 140 | 32 (1) | 44.9 (100) |
| 4. μBondapak C$_{18}$(acetonitrile) | 0.202 | 1,628 | 8,059 | 1,832 (57) | 36.0 (80.1) |
| 5. μBondapak C$_{18}$(1-propanol) | 0.0015 | 1,476 | 984,000 | 223,636 (6,988) | 32.6 (72.6) |

[a]Total protein was determined using bovine serum albumin as a standard. The quantitation of step 5 hTGFs was based on amino acid analysis. The absolute specific activity of a companion aliquot was found to be $1-1.5 \times 10^6$ units/mg.
[b]One EGF-competing activity unit is defined as the amount of protein that inhibits the binding of $^{125}$I-EGF to its receptor by 50%.

To remove serum proteins, A2058 cells were extensively washed with Waymouth's medium prior to their culture in serum-free medium. The supernatant fluids were collected every other day for a 2-week period. Culture conditions were such that at the end of the culture period more than 90% of the cells were still viable and attached as monolayers. The initial clarified A2058-conditioned medium of 136 liters, containing 1.02 g of total protein and 4525 units of EGF-competing activity, was concentrated to about 900 ml using a hollow fiber concentrator with cartridges of 5000 molecular weight cutoff. The total EGF-competing activity was retained and a recovery above 95% was obtained.

Dialysis of the concentrated A2058-conditioned medium against acetic acid and subsequent centrifugation resulted in 95% recovery of the initial total EGF-competing activity. 18% of the protein was acid-insoluble and was discarded. The acid-soluble. partially purified hTGF was subjected to gel permeation chromatography on Bio-Gel P-10. The column was eluted with 1M acetic acid. The bulk of the contaminating protein was eluted in the exclusion volume of the column and was well separated from the EGF-competing activity and growth-stimulating activity. Two peaks of activity were found to be well resolved from each other. Fractions with both EGF-competing and growth stimulating activity (P-10-A and P-10-B) had apparent molecular weights of 10,500 and 6,800, respectively. Fractions having only one of the two activities were not observed. hTGF-containing fractions were pooled as indicated, lyophilized, and further purified. The larger molecular weight TGF eluted from the column in a broad peak (P-10-A) and appeared to be associated with polypeptides of different sizes. P-10-A contained 46% of the initial EGF-competing activity. The small molecular weight TGF eluted from the column in a sharp peak (P-10-B) and represented 45% of the initial total EGF-competing activity. The cumulative yield of total input EGF-competing activity from step 1 through the gel permeation chromatography step was 91% (Table I). hTGF was eluted as two distinct major peaks that varied quantitatively from one preparation to another. In some preparations of A2058-conditioned medium essentially all the growth-promoting activity was in the hTGFs region.

Purification of hTGFs hTGFs was further purified by reverse phase HPLC. Pool P-10-B, after gel permeation chromatography of the acid-soluble EGF-competing activity of concentrated A2068-conditioned medium on Bio-Gel P-10, was reconstituted in 0.05% trifluoroacetic acid in water, and then chromatographed on a μBondapak C$_{18}$ column. EGF-competing and growth-stimulating activities in soft agar of individual fractions were determined. hTGFs was well separated from the bulk of contaminating protein which eluted at higher concentrations of organic solvent. Fractions containing hTGFs were pooled, lyophilized, and taken for rechromatography. A 57-fold purification of hTGFs after gel permeation chromatography was obtained. 80% of the initial EGF-competing activity in pool P-10-B was recovered (Table I).

Rechromatography of the hTGFs-containing fractions on μBondapak C$_{18}$ support was chosen for the final purification step, since only relatively small losses of EGF-competing activity were observed on these columns. In order to obtain a distinct separation of hTGFs from impurities, it was necessary to use a shallow linear 1-propanol gradient in 0.035% trifluoroacetic acid. A bulk of contaminating peptide material was separated from a well-defined peak of activity. EGF-competing and growth-stimulating activities copurified with a distinct absorbance peak at 13% 1-propanol. Fractions containing hTGFs were pooled and further analyzed. The purification of hTGFs was approximately 7000-fold after gel permeation chromatography with a yield of 33% of the initial total EGF-competing activity. The overall recovery of hTGFs from step 3 through the final reverse phase HPLC step was 73%, and the recovery range per step was 80–100% (Table I).

Characterization of hTGFs

The purity of the final hTGFs preparation was determined by analytical SDS-polyacrylamide gel electrophoresis. The gel was stained with silver. One major polypeptide band, with an apparent $M_r = 7400$, was observed. The same pattern was obtained when samples were electrophoresed under nonreducing conditions indicating that TGF is a single chain molecule.

The receptor reactivity of hTGFs was compared with EGF in the radioreceptor assay. The quantitation of hTGFs was based on amino acid analysis of a companion aliquot. Both hTGFs and EGF competed with $^{125}$I-EGF for the EGF receptor sites of A431 human carcinoma cells. The specific EGF-competing activity of hTGFs was found to $1-1.5 \times 10^6$ units/mg; 1.1 ng of hTGFs or EGF were required to inhibit EGF binding by 50%.

hTGFs enabled normal anchorage-dependent rat kidney cells, clone 49F, to grow in soft agar. The half-maximal response of hTGFs in soft agar was reached with 1 EGF-competing unit, or 1.1 ng of hTGFs, whereas EGF does not stimulate growth of these cells in soft agar even when tested with up to 10 μg.

EXAMPLE II

Larger Scale Production, Purification and Amino Acid Sequencing of Human (hTGF), Rat (rTGF), and Mouse (mTGF) Transforming Growth Factors

A. Experimental Procedures

Source of TGF rTGF, mTGF and hTGF were purified from the serum-free medium conditioned by Fisher rat embryo fibroblasts, FRE CL10, a subclone of FRE 3A (Sacks et al. (1979) *Virology* 97, pp. 231–240), nonproductively transformed by Snyder-Theilen feline sarcoma virus (Snyder et al. (1969) *Nature (Lond)*, 221, pp. 1074–1075), a Moloney murine sarcoma virus-transformed 3T3 cell line, 3B11-IC (Bassin et al. (1970) *Int. J. Cancer* 6, pp. 95–107), and two human metastatic melanoma lines, A2058 (see Example I), and A375 (Girad et al. (1973) *J. Natl. Cancer Inst.* 51, pp. 1417–1423), respectively. Cells were grown in 2-liter plastic roller bottles containing Dulbecco's modified Eagle's medium supplemented with 10% calf serum and subsequently maintained in serum-free Waymouth's medium as described in DeLarco et al. (1978) *Proc. Natl. Acad. Sci. U.S.A.* 75, pp. 4001–4005. Serum-free conditioned medium was collected every 24 h, for a 3-day period, clarified by continuous flow centrifugation, and the supernatant concentrated (Marquardt et al. (1980) *J. of Biol. Chem.* 255, pp. 9177–9181). The concentrate of conditioned medium was the starting material for the purification of TGFs.

Purification of TGF

The TGFs were prepared essentially as previously described in Example I for the purification of the melanoma-derived hTGF. The retentate after ultrafiltration of conditioned medium was dialyzed against 0.1 M acetic acid, and the supernatant, after centrifugation, concentrated by lyophilization and reconstituted in 1 M acetic acid for subsequent gel permeation chromatography on a column (2.5×85 cm) of Bio-Gel P-10 (200–400 mesh, Bio-Rad Laboratories). The column was equilibrated with 1 M acetic acid. Fractions comprising the major EGF-competing activity with an apparent molecular weight of approximately 7,000 were pooled and lyophilized.

The final purification of rTGF, mTGF, and hTGF was achieved by reverse phase HPLC using the chromatography system described in Example I. The separations were performed on a μBondapak $C_{18}$ column (10 μm particle size, 0.39×30 cm, Waters Associates). The mobile phase was 0.05% trifluoroacetic acid and the mobile phase modifier was acetonitrile containing 0.045% trifluoroacetic acid. The concentration of acetonitrile was increased linearly (0.083%/min) during 2 h at a flow rate of 1 ml/min at 40° C. for elution of peptides. TGF-containing pools were lyophilized and reconstituted in 0.05% trifluoroacetic acid and rechromatographed on the same column. using as the mobile phase modifier 1-propanol containing 0.035% trifluoroacetic acid. The 1-propanol concentration was increased linearly (0.05%/min) during 2 h at a flow rate of 1 ml/min at 40° C. Pools of fractions comprising the major EGF-competing activity were lyophilized.

Assay for TGF

TGF was quantitated in a radioreceptor assay based on receptor cross-reactivity with mouse submaxillary gland epidermal growth factor (mEGF). Purified mEGF was labeled with Na $^{125}$I by a modification of the chloramine-T method as described in Example I. The $^{125}$I-EGF binding assay was performed on formalin-fixed A431 human carcinoma cells, $8 \times 10^3$, in Micro Test II plates (Falcon). The concentration of TGF was expressed in mEGF ng equivalents/ml and was based on the amount of TGF required to produce equal inhibition of $^{125}$I-EGF binding to A431 cells as a known amount of unlabeled mEGF.

Amino Acid Sequence Determination of TGF

For amino acid sequence analysis. rTGF (3 μg) was reduced with dithiothreitol (20 mM) in 100 μL of Tris-HCl buffer (0.4 M) containing guanidine-HCl (6) and Na$_2$-EDTA (0.1%), pH 8.5, for 2 h at 50° C., and subsequently S-carboxamidomethylated with iodoacetamide (45 mM) for 30 min at 22° C. The S-carboxamidomethylated rTGF was desalted on a μBondapak $C_{18}$ column. Peptide was eluted with a gradient of aqueous acetonitrile containing 0.045% trifluoroacetic acid. The concentration of acetonitrile was increased linearly (1%/min) during 1 h at a flow rate of 1 ml/min at 40° C.

Automated sequence analyses (Edman et al. (1967) *Eur. J. Biochem.* 1, pp. 80–91) of S-carboxamidomethylated rTGF and unmodified mTGF and hTGF were performed with a gas-liquid solid phase microsequenator (Hewick et al. (1981) *J. of Biol. Chem.* 256, pp. 7990–7997). Sequenator fractions were analyzed by reverse phase HPLC (Hunkapiller et al. (1983) *Science* 219, pp. 650–659).

B. Results

Purification of TGF

Purified preparations of a small molecular weight rTGF, mTGF and hTGF were obtained from the conditioned medium of retrovirus-transformed rat and mouse fibroblasts and two human melanoma cell lines, respectively. The purification was achieved by gel permeation chromatography of the acid-soluble EGF-competing activity on Bio-Gel P-10 in 1 M acetic acid, followed by reverse phase HPLC on μBondapak $C_{18}$ support using sequentially a linear gradient of aqueous acetonitrile and subsequently 1-propanol containing 0.035% trifluoroacetic acid. The elution patterns of the final purification step of rTGF. mTGF and hTGF show that EGF-competing activity co-purified with a distinct absorbance peak, and was effectively separated from contaminating UV-absorbing material. The major protein peak of rTGF, mTGF and hTGF preparations eluted from a μBondapak $C_{18}$ column under standard conditions between 48 and 55 min.

Gel permeation chromatography on Bio-Gel P-10 provided a separation of the small molecular weight TGFs from larger molecular weight TGFs and reduced the load of protein applied to a μBondapak $C_{18}$ column in the following purification step. The small molecular weight TGFs represented 45 to 80% of the initial total EGF-competing activity. Reverse phase HPLC of TGFs on μBondapak $C_{18}$ support in the following two purification steps was very efficient, each giving in a typical preparation a recovery range of 80 to 100% per step. The final recovery of the small molecular weight TGFs was approximately 70%. based on the maximal total EGF-competing activity detected during the course of the purification. The average yield of purified rTGF was 90 ng/liter, of mTGF 50 ng/liter and of hTGF 10 ng/liter of conditioned medium. This calculation is based on the specific activity determined for isolated TGFs and on the assumption that the EGF-competing activity measured in the radioreceptor assay reflects levels of total large and small molecular weight TGFs only. No immunoreactive mEGF was detected in conditioned medium.

Purity of TGF

The purity of rTGF, mTGF and hTGF, suggested by the chromatographic elution profiles. was assessed in the EGF radioreceptor assay and by amino acid sequence analysis. rTGF, mTGF and hTGF competed with $^{125}$I-EGF for the EGF receptor sites on A431 human carcinoma cells and were qualitatively and quantitatively nearly indistinguishable from mEGF. Hence, the final TGF preparations were believed to be highly purified and essentially at homogeneity. A single amino-terminal sequence was determined by automated Edman degradation for rTGF, mTGF and hTGF. Any unblocked minor peptide sequence present at >5% could have been detected by the methods used. The homogeneity of hTGF was confirmed in addition by analytical SDS-polyacrylamide gel electrophoresis. The purified preparation gave one major polypeptide band.

Amino Acid Sequencing of TGF

The complete sequencing of the rTGF, mTGF and hTGF was accomplished and the amino acid sequences for the three polypeptides are given below. It will be noted from the sequences reported that rTGF and mTGF are identical in chemical make-up and further that substantial homology exists between the murine TGFs and hTGF with different amino acid residues occurring at only limited positions in the sequences.

rTGF

```
                5                       10         (1)
Val—Val—Ser—His—Phe—Asn—Lys—Cys—Pro—Asp—

15                      20
—Ser—His—Thr—Gln—Tyr—Cys—Phe—His—Gly—Thr—

25                      30
—Cys—Arg—Phe—Leu—Val—Gln—Glu—Glu—Lys—Pro—

35                      40
—Ala—Cys—Val—Cys—His—Ser—Gly—Tyr—Val—Gly—

45                      50
—Val—Arg—Cys—Glu—His—Ala—Asp—Leu—Leu—Ala
``` mTGF

```
                5                       10         (2)
Val—Val—Ser—His—Phe—Asn—Lys—Cys—Pro—Asp—

15                      20
—Ser—His—Thr—Gln—Tyr—Cys—Phe—His—Gly—Thr—

25                      30
—Cys—Arg—Phe—Leu—Val—Gln—Glu—Glu—Lys—Pro—

35                      40
—Ala—Cys—Val—Cys—His—Ser—Gly—Tyr—Val—Gly—

45                      50
—Val—Arg—Cys—Glu—His—Ala—Asp—Leu—Leu—Ala
``` hTGF

```
                5                       10         (3)
Val—Val—Ser—His—Phe—Asn—Asp—Cys—Pro—Asp—

15                      20
—Ser—His—Thr—Gln—Phe—Cys—Phe—His—Gly—Thr—

25                      30
—Cys—Arg—Phe—Leu—Val—Gln—Glu—Asp—Lys—Pro—

35                      40
—Ala—Cys—Val—Cys—His—Ser—Gly—Tyr—Val—Gly—

45                      50
—Ala—Arg—Cys—Glu—His—Ala—Asp—Leu—Leu—Ala
```

EXAMPLE III

Production of TGF in Vivo and its Isolation

Tumor cell lines (1×10⁶) known to produce TGFs (human melanoma and transformed rat) were inoculated into athymic "nude" mice and tumors were allowed to develop. The urine from the tumor-carrying mice was collected and analyzed for the presence of TGF using the isolation procedure and analytical techniques given in Example I above. TGF was detected in the urine of the tumor carrying mice which has the same size and elution properties on HPLC as does the cell culture derived TGF which is described in Examples I and II above. Further, using the procedures described in Example I above, the TGF present in the mouse urine was found to have the characteristic TGF biological properties, in that it stimulates anchorage-independent growth of cells and binds to the EGF receptor. Subsequently, the tumors were removed from the tumor-carrying mice and the urine of the mice after tumor removal were tested for the presence of TGF using the above mentioned procedures. In this case, no TGF was found having the characteristic elution properties on HPLC or TGF-like biological activity. These results demonstrate that tumor cells produce TGF in whole animals as well as cell cultures and that TGF can be detected in and isolated from body fluids using the process of the invention. Similar experiments were also performed with rats having chemical carcinogen-induced tumors and they were found to have TGF in their urine, based on the biological and biochemical properties listed above, while untreated rats did not.

EXAMPLE IV

Inhibition of Retroviral Transformed Cell Growth In Vitro with Antibodies to Antigenic TGF Oligopeptide An oligopeptide having the following amino acid sequence (which corresponds to amino acid sequences 34 through 50 of rat TGF):

Cys-His-Ser-Gly-Tyr-Val-Gly-Val-Arg-Cys-Glu-His-Ala-Asp-Leu-Leu-Ala was synthesized using the solid-phase technique of Ohgak et al. (1983) *Journal of Immunol. Meth.* 57, pp. 171–184. This oligopeptide was then coupled to keyhole limpet hemocyanin in accordance with the procedure of Baron et al. (1982) *Cell* 28, pp. 395–404, and used to immunize rabbits (Baron et al. (1982) *Cell* 28, pp. 395–404) and sheep (Lerner (1982) *Nature* 299, pp. 592–596). Antisera were assayed against peptide by a peroxidase-linked immunoassay (Kirkegaard and Perry Laboratories, Gaithersberg, Md.) and against homogeneous rat TGF (purified according to Example II above), by immunoprecipitation (Bister et al. (1980) *J. Virol.* 36, pp. 617–621) and Western blotting techniques (Burnett (1981) *Analyt. Biochem.* 112, pp. 195–203). Binding of $^{125}$I-labeled rat TGF and mouse EGF (Bethesda Research Labs, Bethesda, Md.) to A431 cells grown in 96-well microtiter plates was as described in Pross et al. (1977) *Proc. Natl. Acad. Sci. U.S.A.* 74, pp. 3918–3921.

Antisera prepared in one rabbit and two sheep reacted with the corresponding peptide in peroxidase-linked immunoassays in titers of at least $10^4$. Reactions of the rabbit antiserum with rat TGF were documented by immunoprecipitation and confirmed by Western blotting. The antipeptide antisera did not immunoprecipitate iodinated mouse EGF in this study.

Human epidermoid carcinoma A431 cells have in excess of $10^6$ EGF receptors per cell (Fabricant et al. (1977) *Proc. Natl. Acad. Sci. U.S.A.* 74, pp. 565–569). TGF competes with EGF for binding to these receptors. Binding of $^{125}$I-labeled rat TGF to these cells was blocked by an excess of unlabeled EGF and by antiserum to peptide. A blocking effect of antiserum on TGF binding was observed even if the antibody-TGF complex was not removed from the medium surrounding the A431 cells by *S. aureus* protein A-facilitated immunoprecipitation. Blocking by the antibody was a result of interaction with the TGF molecule rather than with the receptor, since antisera did not react in immunoprecipitation assays with purified iodinated EGF receptor. As anticipated from immunoprecipitation data, antiserum to peptide did not interfere with binding of murine EGF to A431 cells.

With the availability of antisera that blocked cellular binding of TGF but not EGF, it was possible to test whether TGF functions by an autocrine mechanism, stimulating the growth of malignant cells, and whether antibody can thus inhibit such growth in vitro. Consequently, untransformed normal rat kidney cells (NRK) and a variety of retroviral cell lines were plated at low densities (500 to 2.000 cells per dish) in serum-containing medium and after a brief period of adherence were switched to serum-free medium. Sheep or rabbit antibodies to TGF peptide or to various irrelevant non-crossreacting peptides were added to the medium, and the effect on cell growth, on microscopic and macroscopic colony formation, and on colonial morphology was observed. All antibodies were affinity purified on peptide columns, extensively dialyzed, concentrated, and reconstituted to an antipeptide titer of $10^3$ to $10^4$. The results are provided in Table II below.

TABLE II

EFFECT OF ANTIPEPTIDE ANTIBODIES ON GROWTH OF CELLS IN VITRO

| Antibody | Source | Volume (μl) | Other Addition | % Inhibition of Colony Formation by | | | |
|---|---|---|---|---|---|---|---|
| | | | | NRK cells | CL10 cells | Ki-NRK | src-3T3 |
| Anti-TGF oligopeptide | Rabbit | 5 | — | 0 | 85 | NT | 53 |
| | | 5 | TGF peptide | NT | 36 | NT | 6 |
| Anti-TGF oligopeptide | Sheep | 2 | | 0 | 50 | 49 | NT |
| | | 5 | | 0 | 68 | 85 | 77 |
| | | 10 | | 0 | 79 | 73 | 100 |
| | | 5 | TGF peptide | NT | 9 | 20 | 43 |
| | | 5 | Irrelevant peptide | NT | 85 | NT | NT |
| Anti-hetero peptides | Sheep & rabbit | | | 0 | <15 | ≦5 | 0 |

As seen in Table II above, neither rabbit nor sheep anti-TGF oligopeptide inhibited colony formation by NRK cells, but within 48 hours inhibited growth of Kirsten-transformed NRK cells, feline-sarcoma-virus-transformed rat embryo fibroblasts (CL10 cells), and Rous-sarcoma-virus-transformed 3T3 cells. (CL10 cells are known to be prolific producers of TGF (Marquardt et al. (1983) *Proc. Natl. Acad. Sci. U.S.A.* 80, pp. 4684–4688)). The few surviving colonies in anti-TGF antibody-treated cells tended to be smaller and lacked the robust appearance of normal colonies. Non-adherent unlysed cells floated free in the medium. This inhibition was partially reversed when TGF peptide, but not non-cross-reacting irrelevant peptide, was added concomitantly with antibody to TGF. Rabbit and sheep antibodies to four different non-cross-reacting peptides had no effect on growth of colonies of NRK or retroviral transformed cell lines. Replacement of antibody-containing medium by fresh antibody-free medium after 72 hours failed to reverse the inhibition of colony formation, but the surviving colonies grew vigorously.

EXAMPLE V

Synthesis and Characterization of rat TGF

The chemical synthesis of rat TGF, having the chemical formula given in Example II, was performed manually by the stepwise solid-phase approach according to the general principles described by Merrifield (1963) *J. Amer. Chem. Soc.* 85, pp. 2149–2156. The differential acid-labile protecting group strategy was adopted for this synthesis with the conventional combination of tertbutyloxycarbonyl for N-amino terminus and benzyl alcohol derivatives for the side chains. A more acid stable benzyl ester linkage that anchored protected amino acids to the polymeric support was used to minimize loss of peptides during the repetitive acid treatments (Mitchell et al. (1976) *J. Amer. Chem. Soc.* 92, pp. 7357–7362). Complete deprotection and removal of peptide from the resin was by the low-high HF method of Tam et al. (1983) *Tetrahedron Lett.* 23, pp. 4435–4438, which differed from the conventional HF deprotection method and removed benzyl protecting groups by the $S_N2$ mechanism in dilute HF solution to minimize serious side reactions due to carbocations generated in the conventional $S_N1$ deprotection method. Furthermore, it is also designed to reduce many cysteinyl side reactions that often hamper the synthesis of proteins containing multiple disulfide linkages.

After HF treatment and prior to any purification, the crude and reduced synthetic rTGF was oxidized and regenerated by the mixed disulfide method in the presence of a combination of reduced and oxidized glutathione (Ahmed et al. (1975) *J. Biol. Chem.* 250, pp. 8477-8482). This avoided the formation of polymeric materials during purification. The regenerated, crude rTGF contained 40-50% of EGF-radioreceptor and tyrosine-specific protein kinase activities when compared to the natural rTGF. Crude synthetic rTGF was purified to homogeneity in three steps: (1) gel filtration on a Bio-Gel P-10 column; (2) ion-exchange chromatography on a CM-Sephadex column; and (3) preparative high pressure liquid chromatography on a $C_{18}$ reverse phase column. An overall yield, based on starting loading of Ala to resin, was 31%.

Under reducing or nonreducing conditions, the purified synthetic rTGF was found to give a single band with an apparent molecular weight of 7000 on SDS-PAGE electrophoresis. Amino acid analysis by 6N HCl and enzymatic hydrolysis provided the expected theoretical molar ratio of the proposed sequence. No free thiol was detected by Ellman's method of sulhydryl determination on synthetic rTGF, but upon thiolytic reduction, the expected theoretical value of six cysteines was obtained. These findings support the conclusion that synthetic rTGF is a single chain polypeptide containing six cysteines in disulfide linkages, which is in agreement with the expected chemical properties of the natural rTGF. Additionally, synthetic rTGF coeluted with the natural rTGF as a single symmetrical peak in $C_{18}$ reverse phase HPLC.

Synthetic rTGF prepared in accordance with this Example was compared with natural rTGF in three assays for biological properties of the putative transforming growth factor. In the mitogen assay, the stimulation of growth of serum-deprived normal rat kidney cells by rTGF was measured by the incorporation of $^{125}$I-Iododeoxyuridine. In the soft agar assay in the presence of fetal bovine serum and a second TGF, TGF-beta, the morphological and phenotypic alterations by rTGF could be quantitated by colony formation in soft agar. The latter transforming assay has been shown to correlate well with tumorigenicity (Stoker et al. (1968) *Int. J. Cancer* 3, pp. 683-693). Fetal bovine serum or TGF-beta alone does not induce transformation of NRK cells in culture. Similarly, TGF, natural or synthetic, does not produce such an effect in the absence of TGF-beta. Both synthetic and natural rTGF displayed similar dose response curves and half maximal activities in these two assays.

Since rTGF competes with mEGF for the binding of EGF receptors on cellular membranes, synthetic rTGF was compared with the natural rTGF for binding on A431 human carcinoma cells. Again, the response and activities of the natural and synthetic rTGF were found to be indistinguishable from each other. The concentration required for 50% inhibition of $^{125}$I-EGF binding was found to be 3.5 and 4.1 nM for the natural and synthetic rTGF respectively. A consequence of TGF or EGF binding to the EGF membrane receptors is the stimulation of phosphorylation of tyrosine residues of synthetic peptides or endogenous substrates (Pike et al. (1982) *J. Biol. Chem.* 275, pp. 14628-14631). Synthetic rTGF was found to stimulate the phosphorylation of the synthetic angiotensinyl peptide substrate with a half maximal activity of 0.3 nM, an activity comparable to the value for natural rTGF, reported by Reynold et al. (1981) *Nature* 292, pp. 259-261.

EXAMPLE VI

Wound Healing Using TGFs

Human EGF (hEGF), rat TGF, analog of human TGF, natural vaccinia virus growth factor (VGF) and recombinant VGF were used in a wound healing test, according to the procedure below, to determine the healing effects of each factor on second degree burns. The rat TGF was synthesized as described above in Example V and had the chemical formula given in Example II. The analog of human TGF, which was prepared using standard recombinant techniques, had the following amino acid sequence:

```
                      5                    10
Val—Val—Ser—His—Phe—Asn—Asp—Cys—Pro—Asp—

15                    20
—Ser—His—Thr—Gln—Phe—Cys—Phe—His—Gly—Thr—

25                    30
—Cys—Arg—Ser—Leu—Val—Gln—Glu—Glu—Lys—Pro—

35                    40
—Ala—Cys—Val—Cys—His—Ser—Gly—Phe—Val—Gly—

45                    50
—Val—Arg—Cys—Glu—His—Ala—Asp—Leu—Leu—Ala
```

Natural VGF was purified as described below in Example XV. Recombinant VGF was also produced using standard recombinant techniques. The natural VGF is a 25 kd protein containing the following amino acid sequence which falls within the scope of formula I above:

```
                      5                    10
Leu—Cys—Gly—Pro—Glu—Gly—Asp—Gly—Tyr—Cys—

15                    20
—Leu—His—Gly—Asp—Cys—Ile—His—Ala—Arg—Asp—

25                    30
—Ile—Asp—Gly—Met—Tyr—Cys—Arg—Cys—Ser—His—

35                    40
—Gly—Tyr—Thr—Gly—Ile—Arg—Cys—Gln—His—Val—

—Val—Leu—Val
```

The full amino acid sequence for the VGF molecule purified as described below in Example XV (and that expressed via recombinant technique) is as follows:

```
                      5                    10
Asp—Ser—Gly—Asn—Ala—Ile—Glu—Thr—Thr—Ser—

15                    20
—Pro—Glu—Ile—Thr—Asn—Ala—Thr—Thr—Asp—Ile—

25                    30
—Pro—Ala—Ile—Arg—Leu—Cys—Gly—Pro—Glu—Gly—

35                    40
—Asp—Gly—Tyr—Cys—Leu—His—Gly—Asp—Cys—Ile—

45                    50
—His—Ala—Arg—Asp—Ile—Asp—Gly—Met—Tyr—Cys—

55                    60
—Arg—Cys—Ser—His—Gly—Tyr—Thr—Gly—Ile—Arg—
```

-continued

```
                       65                      70
—Cys—Gln—His—Val—Val—Leu—Val—Asp—Tyr—Gln—

75                          80
—Arg—Ser—Glu—Asn—Pro—Asn—Thr—Thr—Thr—Ser—

85                            90
—Tyr—Ile—Pro—Ser—Pro—Gly—Ile—Met—Leu—Val—

95                       100
—Leu—Val—Gly—Ile—Ile—Ile—Ile—Thr—Cys—Cys—

105
—Leu—Leu—Ser—Val—Tyr—Arg—Phe—Thr—

110
                        —Arg—Arg—Thr
```

Three female piglets of approximately 10 pounds each were anesthetized with Ketamine and Rompum and their backs were shaved and the remaining hair was totally removed with a commercial depilatory cream. A brass template (3×3 cm, 147 gm) was equilibrated in a 70° C. water bath and then placed in firm contact with the bare skin for exactly 10 seconds. Five wounds were placed on each side of the spine and were separated from each other by approximately 1 inch. The top of each resulting blister was totally removed and the wounds were treated twice a day with Silvadene alone, Silvadene containing one of the growth factors, or left untreated. The piglets were allowed to eat and drink at will.

After 9 or 10 days, the piglets were anesthetized and the eschar from each burn was removed. All burns were photographed and a punch biopsy was taken within each burn.

The following table indicates the approximate percentage of each burn that was epithelialized using visual judgment.

TABLE III

Pig 1
9 Days Post-Burn

|  | Silvadene | Untreated | Natural VGF μg/ml | | |
|---|---|---|---|---|---|
|  |  |  | 0.1 |  | 0.1 |
| Right Side | 15% | 0% | 70% |  | 65% |
|  |  |  | hEGF μg/ml | | |
| Left Side | Silvadene | Untreated | 0.1 | 0.1 | 0.1 |
|  | 75% | 55% | 60% | 70% | 30% |

Pig 2
10 Days Post-Burn

|  | Silvadene | Untreated | Recombinant VGF μg/ml | | |
|---|---|---|---|---|---|
|  |  |  | 0.1 | 0.5 | 1.0 |
| Right Side | 50% | 0% | 95% | 95% | 60% |
| Left Side | Silvadene | Untreated | 0.1 | 0.5 | 1.0 |
|  | 50% | 0% | 60% | 75% | 40% |

Pig 3
9 Days Post-Burn

|  | Silvadene | Untreated | Rat TGF μg/ml | | |
|---|---|---|---|---|---|
|  |  |  | 0.1 | 0.5 | 10 |
| Right Side | 20% | 15% | 90% | 65% | 90% |
|  |  |  | Analog of Human TGF μg/ml | | |
| Left Side | Silvadene | Untreated | 0.1 | 0.5 | 10 |
|  | 25% | 5% | 90% | 85% | 65% |

As shown in Table III, the TGFs were very effective in healing wounds, when compared to the untreated controls or even when compared to Silvadene alone.

EXAMPLE VII

Wound Healing

Another experiment was performed to measure the effect of the analog of human TGF described above on the healing of second degree burns. The experimental conditions were similar to those described above. However, the following changes were made in the procedures. One Yorkshire piglet was anesthetized with Ketamine and each of 12 burns was made using the template for 11 seconds per burn. After each blister was removed, the wounds were treated once a day with one of the following:

a. 1 μg/ml of TGF in Silvaden
b. 0.1 μg/ml of TGF in Silvadene;
c. untreated;
d. Silvadene alone;
e. 1 μg/ml of hEGF in Silvadene; and
f. 0.1 μg/ml of hEGF in Silvadene.

After 7 days, the eschar was removed. The percentage of wound healing. calculated from planimetry results, is shown below. TGF was very effective as a wound healer.

TABLE IV

| | PERCENTAGE OF WOUND HEALED | |
|---|---|---|
| TREATMENT | Burn A | Burn B |
| TGF 1 μg/ml | 9 | 26 |
| TGF 0.1 μg/ml | 34 | 57 |
| Untreated | 3 | 6 |
| Silvadene | 14 | 21 |
| hEGF 1 μg/ml | 14 | 17 |
| hEGF 0.1 μg/ml | 17 | 14 |

EXAMPLE VIII

Corneal Wound Healing of rTGF

A. Preparation of rTGF polypeptide

The TGF polypeptide was synthesized based on the amino acid sequence reported in Example II above, for TGF purified from the conditioned medium of Fisher rat embryo fibroblasts transformed by feline sarcoma virus. The chemical synthesis of the rTGF was performed as described in Example V above.

B. Preparation of treatment formulation

The rTGF-α polypeptide was combined with isotonic (285 m osmoles) sterile phosphate buffered saline (pH 7.4) at a concentration of 50 ng/ml.

C. Corneal Stromal Incisions

Totally penetrating incisions 5 mm in length, which extended into the anterior chamber along their entire length. were made in the center corneas of adult female *Macaca fasicularis* primates. The right eyes served as controls and were treated three times each day with two drops of isotonic (285 m osmoles) sterile phosphate buffered saline (pH 7.4) without rTGF. The left eyes were treated on the same schedule with the treatment formulation described above. After three days of treatment, the strength of the wounds was quantitatively measured by inserting a small bore needle (25 gauge) into the anterior chamber through the limbus of the cornea. The needle was connected to an aneroid manometer, and the pressure was slowly and steadily increased until the wounds first began to leak. and then burst. This procedure is described in detail by Weene (1983) *Anal. Ophthalmol.* 15, 438.

D. Results

The results shown in Table V demonstrate that the bursting strength of TGF treated corneas is significantly stronger than the saline treated control corneas.

TABLE V

| | mm of Hg | | | |
|---|---|---|---|---|
| | Control Right Eye | | TGF-treated Left Eye | |
| | Leak | Burst | Leak | Burst |
| Monkey P-21 | 25 | 30* | 210 | 225* |
| Monkey P-20 | 35 | 90* | 155 | >300* |

*t = 40.0, p < 0.025, paired T-test.

EXAMPLE IX

In vivo Studies with anti-TGF Antibody

An anti-TGF serum was prepared by immunizing a rabbit with a glutaradehyde conjugate of the 17-amino acid sequence of rTGF described in Example IV above, and KLH (keyhole limpet hemocyanin), then the Ig fraction was prepared by precipitating the serum twice with a 45% saturated solution of ammonium sulfate, redissolving it to the original volume, and dialyzing against PBS.

The anti-TGF serum and a control serum were diluted from their original volume of 0.5 ml to 3 ml. The resulting volumes were used to inject mice intraperitoneally at a dosage of 0.1 ml per mouse. Ten mice, about 3 months old, were each previously subcutaneously transplanted with two small pieces of a rat tumor derived from the Snyder-Theilen feline sarcoma virus. (Each transplant was counted as one site, which results in 20 total sites with 10 sites for the control group and 10 sites for the treated group.) The mice were injected starting the day after the transplant and also were injected on days 4, 7 and 11.

Starting on the seventh day, tumor diameters were measured in two directions with calipers. The tumors were measured at regular intervals on days 9, 11, 14, 16, 18, and 24.

At the time of the first measurement, 7 of the 10 sites for the control group had evidence of tumor growth, while only 4 of the 10 sites for the treated group had tumor growth. In addition, 6 of the 10 sites in the control group had tumors that were at least 3 mm in diameter, while only 3 sites in the treated group had tumors of that size. Four sites in the control group were at least 5 mm in diameter on day 9, while only 2 sites in the treated group were that size. By day 11, the control group and the experimental group had similar tumors.

EXAMPLE IX

Detection of TGF Activity in Urine of Cancer Patients

Various samples of urine were pretreated at 90° C. for one minute after adding 1/9 volume of 20% SDS, 0.4 M DTT, 0.4 M Hepes, 0.08 M sodium chloride, 1 mM EDTA, to a pH of 7.4. A 20 μL sample was added to an incubation mixture (50 μL total) modified to contain 1% NP-40. Incubation of sample, antibody raised to the 17-amino acid sequence of rat TGF in Example IV and $^{125}$I-labelled synthetic 17-amino acid sequence was performed in 96 well plates for 60 minutes, followed by 30 minutes with Pansorbin. Antibody-bound peptide was pelleted on a cushion of dibutyl phthalate and pellets were counted in a gamma counter using ⅛ inch thick lead sleeves to shield the unpelleted isotope.

TGF levels were standardized using the synthetic sequence and human melanoma (A375 cell line) TGF from concentrated serum-free conditioned culture medium. TGF levels were calculated as ng of TGF per mg of creatinine. In each experiment, one or more normal samples were assayed and the average normal value was assigned a value of one Relative TGF Equivalent.

A. Sample Preparation

Fresh, unclarified urine samples were stored in 25 ml aliquots at −70° C. for up to six months. In most cases, the samples were rapidly thawed and immediately treated with protease inhibitors (0.5 mM phenylmethylsulfonyl fluoride, 0.05 mM pepstatin A, Sigma Chemical Co.) for 30 minutes at 4° C. Ten ml samples were then dialyzed at 4° C. against either 0.1 M acetic acid or 0.1 M ammonium bicarbonate. Dialysis tubing with three different pore sizes was used: 3,500; 6,000-8,000; or 12,000-14,000. (In some cases, the urine was initially lyophilized and extracted, but the neutralization and ethanol/ether precipitation steps were omitted.)

After 2 to 4 days of dialysis, the urines were clarified (10,000×g for 10 minutes), lyophilized, redissolved at 50 times the original concentration in 5 mM formic acid, and 50 mM sodium chloride, then clarified briefly (12,000×g, one minute) prior to pretreatment.

B. Creatinine Assays

An untreated aliquot of each sample was tested in duplicate for creatinine, using a manual colorimetric test.

C. Results

The samples were standardized for creatinine levels. For each of 6 experiments, statistical analysis (T-test) indicated significant differences between cancer patients and normals (P<0.001, 0.001, 0.001, 0.001, 0.01, 0.05). In the six experiments, TGF concentration in urines from normal individuals averaged 0.18 ng of TGF per mg of creatine, while the urines from all cancer patients averaged 0.64 ng of TGF. Elevated levels of TGF was observed in most cancer patients. Results in each experiment were also normalized relative to the average normal value in that experiment. Data are expressed numerically in Table VI. Using an arbitrary cutoff of twice the average normal level of TGF, in 81% of the various cancers tested, higher than normal TGF levels were detected.

TABLE VI

| DETECTION OF ALPHA TGF ANTIGEN IN URINE | | | | | |
|---|---|---|---|---|---|
| | | SAMPLE PROCESSING PH AND RIA CONCENTRATION FACTOR | | | |
| | OVERALL | pH 2 | | pH 8 | |
| PATIENT GROUP | POSITIVE | 9x | 18x | 9x | 18x |
| Apparently healthy controls | 1/18 (6%) | 0/6 | 1/12 | 1/15 | 0/15 |

TABLE VI-continued
DETECTION OF ALPHA TGF ANTIGEN IN URINE

| PATIENT GROUP | OVERALL POSITIVE | SAMPLE PROCESSING PH AND RIA CONCENTRATION FACTOR | | | |
|---|---|---|---|---|---|
| | | pH 2 | | pH 8 | |
| | | 9x | 18x | 9x | 18x |
| Patients with benign conditions | 1/3 | 0/3 | 1/3 | 0/1 | 0/1 |
| colon (villous adenoma) | 0/1 | 0/1 | 0/1 | | |
| breast (fibrocystic) | 0/1 | 0/1 | 0/1 | 0/1 | 0/1 |
| pregnancy (normal, 38 wks) | 1/1 | 0/1 | 1/1 | | |
| Patients with cancer | 26/32 (81%) | 17/28 (61%) | 22/31 (71%) | 9/16 (56%) | 12/16 (75%) |
| Lung | 11/13 (85%) | 11/13 (85%) | 12/13 (92%) | 3/4 (75%) | 4/4 (100%) |
| Gastrointestinal | 4/7 (57%) | 4/7 (57%) | 4/7 (57%) | 3/7 (43%) | 3/7 (43%) |
| Urogenital | 3/3 (100%) | 1/3 (33%) | 1/3 (33%) | 2/3 (67%) | 3/3 (100%) |
| Breast | 5/5 (100%) | 1/1 (100%) | 5/5 (100%) | | |
| Lymphoid | 3/4 (75%) | 0/4 (0%) | 1/4 (25%) | 2/2 (100%) | 2/2 (100%) |

*Cut off > 2 × average normal value

EXAMPLE X

Detection of TGF Activity in Urine of Cancer Patients

Human urine from 50 people (25 normals and 25 individuals having advanced cancer) was subject to immunoassay using antibody to TGF using the procedure described above in Example IX. In this study, 100 ml of urine from the individuals under test was collected, dialyzed against 1.0 molar acetic acid, and concentrated about 100fold. This concentrated urine was then subject to an immunoassay using rabbit polyclonal antibody raised to the 17 amino acid oligopeptide as in Example IV above, and the results are reported in the table below.

TABLE VII
DETECTION OF TGF ACTIVITY IN URINE OF CANCER PATIENTS

| DIAGNOSIS | NO. POSITIVE/NO. TESTED |
|---|---|
| Lung Cancer | 4/5 |
| Breast Cancer | 4/5 |
| Colon Cancer | 3/5 |
| Melanomas | 5/5 |
| Leukemias | 0/5 |
| Normal Conditions | 1/25 |

In this test, the level of TGF in urine of the majority of cancer patients was at least 5-fold higher than that present in the normal individuals under test.

EXAMPLE XI

Detection of TGF with a Monospecific Antiserum Directed Against a Synthetic Peptide

Peptide Synthesis

Peptides, corresponding to amino acids from portions of rTGF amino acid sequence, described above in Example II, were synthesized commercially (Peninsula Labs) by the standard solid phase technique of Ohgak et al. (1983) *Journal of Immunol. Meth.* 57, pp. 171–184. If necessary, peptides were purified by reverse phase high performance liquid chromatography (HPLC) prior to use. The sequences used were:

Peptide I—Val-Val-Ser-His-Phe-Asn-Lys-Cys-Pro-Asp-Ser-His-Thr
Peptide II—Cys-His-Ser-Gly-Tyr-Val-Gly-Val-Arg-Cys
Peptide III—Cys-His-Ser-Gly-Tyr-Val-Gly-Val-Arg-Cys-Glu-His-Ala-Asp-Leu-Leu-Ala
Peptide IV—Val-Gly-Val-Arg-Cys-Glu-His-Ala-Asp-Leu-Leu-Ala

Peptide Conjugation and Immunization

A sample of peptide (10 mg) was mixed with keyhole limpet hemocyanin (10 mg; Calbiochem) in 3.5 ml of 0.1 M sodium phosphate at pH 7.4. Four milliliters of 25 mM glutaraldehyde was added, and the mixture was incubated, with shaking, for 1 hr at 23° C. Glycine was then added to a final concentration of 0.1 M and the mixture was shaken overnight at 23° C. The resulting conjugate was mixed with an equal volume of Freund's complete adjuvant prior to injection.

Rabbits were immunized by subcutaneous injection of 1 mg of conjugate injected subcutaneously at four separate sites. Two booster injections were administered at bi-weekly intervals following the initial injection. The serum used in this study was collected eighty days after the initial injection. An immunoglobulin fraction of this serum was prepared by ammonium sulfate precipitation. The product of antibodies specific for immunizing peptide was monitored with a solid phase enzyme-linked immunoabsorbent assay.

Radioiodination of Peptides

Peptides were labeled with $Na^{125}I$ using the chloramine-T procedure, essentially as described in Das et al. (1977) *Proc. Natl. Acad. Sci.* 74 pp. 2790–2794. Solutions containing mouse submaxillary gland EGF (mEGF) (170 p moles), synthetic rTGF (4 p moles) or peptide III (400 p moles) were mixed with 1–2 mCi $Na\,^{125}I$ (Amersham, 2 mCi/n mole) in 2 M potassium phosphate at pH 7.5. Chloramine T (50–100 μg) was added and incubation at 4° was continued for 1 minute (mEGF and rTGF) or 7 minutes (peptide III). Reactions were terminated by the addition of $Na_2S_2O_5$ (10–20 μg) and labeled proteins were separated from unreacted $Na^{125}I$ by chromatography on Sephadex G-10 (Pharmacia). Specific activities of peptides labeled in this fashion were: $1 \times 10^{10}$ cpm/n mole (EGF); $6 \times 10^8$ cpm/n mole (rTGF): and $1 \times 10^9$ cpm/n mole (peptide III).

Radioreceptor Assay

The binding of $^{125}$I-EGF to its receptor on monolayers of formalin-fixed A431 cells was measured as described above in Example I. $^{125}$I-EGF was added at a final concentration of 0.33 nM in the presence or absence of competing substances. Addition of unlabeled EGF at 0.3-0.5 nM resulted in half-maximal inhibition of $^{125}$I-EGF binding. TGF concentrations were expressed as the amount required to produce an inhibition of $^{125}$I-EGF binding. equivalent to a known amount of TGF.

Radioimmunoassay

Reactants were mixed in a final volume of 50 microliters of a solution containing: 20 mM sodium phosphate, at pH 7.4; 200 mM NaCl: 40 mM dithiothreitol; 0.1% (w:v) BSA; 0.1% (w:v) NaN$_3$: $^{125}$I-peptide III; ($10^4$ cpm); antiserum at a final dilution of 1/15,000; and other additions, as specified. The reaction was initiated by the addition of antiserum and continued at 23° C. for 90 minutes. An equal volume of 10% formalin-fixed Staphalococcus A (Pansorbin, Calbiochem) was then added and incubation was continued for an additional 30 minutes at 23° C. The immunoadsorbant was removed by sedimentation through a cushion of 10% (w:v) sucrose and the amount of bound $^{125}$I-peptide III was determined using a gamma counter. Under these conditions, approximately 25% of $^{125}$I-peptide was bound by antibody in the absence of competitor. The amount of bound peptide III was corrected for non-specific binding measured in the absence of antibody (less than 5% of the total) and expressed as a percentage of maximal binding. Concentrations of competitors were expressed as the amount of peptide III required to give an equivalent inhibition of precipitation.

Chromatography

Gel filtration chromatography was performed according to the manufacturer's instructions on columns of Bio Gel P-10 (BioRad) equilibrated in 1 N acetic acid. HPLC was performed on a Novapak C$_{18}$ column (0.39×10 cm; Waters Associates) using a flow rate of 1 ml/min at 23° C.

Preparation of Conditioned Medium

Serum-free conditioned medium from Snyder Theilen-transformed Fischer rat embryo cells (ST-FrSV-FRE clone-10) was collected as previously described in Twardzik et al. (1983) *Virology* 124, pp 201-207. The medium was clarified by low speed centrifugation and lyophilized. The residue was then resuspended in 1 N acetic acid and dialyzed extensively against 0.1 N acetic acid. Insoluble protein was removed by centrifugation and the supernatant was lyophilized. Finally, the residue was resuspended in one-hundredth the original volume of 1 N acetic acid and stored at 4° C.

Immunoblotting Analysis

Samples to be analyzed were first subjected to sodium dodecyl sulfate polyacrylamide gel electrophoresis (SDS-PAGE) on a 15-20% acrylamide gradient. and then run under reducing conditions, using the system described by Laemmli (1970) *Nature* 227, pp. 680-682. Following separation, proteins were electrophoretically transferred to nitrocellulose (Schleicher and Schuell, BA85, 0.45 u) as described by Burnette (1981) *Anal. Biochem.* 112, pp. 195-203. Transfer was accomplished at approximately 5 V/cm for a period of 3-4 hours at 23° C. The resultant protein blot was incubated overnight in a milk-based cocktail, BLOTTO (Johnson et al. *Gene Anal. Techn.* 1, pp. 3-8). Antiserum was diluted in BLOTTO and added to the blot in the presence or absence of excess peptide III. Incubation with antibody was continued with frequent agitation for 2-3 hours at 23° C. The blot was then washed and incubated with $^{125}$I-protein A ($4 \times 10^6$ cpm/ml: $4 \times 10^7$ cpm/μg) for one hour at 23° C., and washed with BLOTTO. Antibody binding sites were visualized following autoradiography on Kodak XAR-5 film at −70° C. using intensifying screens.

Results

Using the radioimmunoassay described above, input $^{125}$I-peptide III was nearly quantitatively precipitated at low dilution of antisera; the antiserum showed a titer of >10,000. Antibody affinity was measured by incubating the antiserum at a final dilution of 1/5,000 with varying concentrations of $^{125}$I-peptide III. Analysis of these data by the method of Scatchard revealed a single class of binding component(s) having an affinity constant (Ka) of $8.3 \times 10^8$ M$^{-1}$ for $^{125}$I-peptide III.

Specificity of Radioimmunoassay

To determine the specificity of the radioimmunoassay, various peptides were tested for their ability to inhibit precipitation of $^{125}$I-peptide III. Unlabeled peptide III inhibited the precipitation of $^{125}$I-peptide-III in an approximately linear fashion in the range of 0.13 to 11 nM; the concentration of unlabeled peptide III, which produced half-maximal inhibition of precipitation, was 0.7 nM. Peptide IV was only slightly less effective an inhibitor of precipitation than was peptide III, while peptide II was totally ineffective at concentrations up to 1.1 uM. Peptide I, corresponding to the amino terminal 11 residues, also was ineffective as a competitor. These results indicate that the epitope detected under standard assay conditions was localized to the carboxy-terminal 11 amino acids of peptide III. A summary of the relative inhibitory concentrations of various peptides is presented in Table VIII.

TABLE VIII

| Addition | Relative Inhibitory Activity |
| --- | --- |
| PeptideIII | 1 |
| Peptide IV | 3.5 |
| Peptide I | >1500 |
| Peptide II | >1500 |
| rTGF + dithiothreitol | 1 |
| rTGF − dithiothreitol | 20 |
| mEGF | >1500 |

The indicated additions were tested for their ability to inhibit the standard RIA as described above. The concentration of each addition necessary to achieve half-maximal inhibition of precipitation was determined and is expressed relative to the concentration of peptide III required to give the same level of inhibition. The symbol ">" indicates the highest concentration tested. (The inhibitory activities of peptides I–IV were unaffected by the inclusion of diethiothreitol in the assay.)

rTGF was also tested for its ability to inhibit precipitation of $^{125}$I labeled peptide III. Synthetic rTGF, which was indistinguishable from the native molecule in biologic activity, was equally effective (on a molar basis) an inhibitor as was peptide 111. The relative inhibitory capacity of rTGF was considerably diminished when a reducing agent was omitted from the reaction mixture (Table). mEGF was totally ineffective as a competitor, at concentrations ranging up to greater than 1 μM. This indicates that the RIA described here differs from other available assays for TGF in that it is specific for TGF, but not EGF.

In order to show directly that the antiserum binds rTGF, $^{125}$I-labeled rTGF was substituted for $^{125}$I-peptide III in the standard RIA. A dose dependent precipitation of $^{125}$I-TGF was observed, which was inhibited substantially by the addition of excess unlabeled peptide III. Scatchard analysis of the binding data obtained in this fashion indicated that the antiserum exhibited a $K_a$ of $2.3 \times 10^8$ M$^{-1}$ for $^{125}$I-TGF. This value was in reasonable agreement with the $K_a$ determined for $^{125}$I-peptide III ($8.3 \times 10^8$ M$^{-1}$) and indicated that the antiserum binds to rTGF.

Detection of rTGF in Conditioned Medium of Transformed Cells

One source of TGF is the culture medium of cells transformed by RNA tumor viruses. In order to detect rTGF in conditioned medium from cultured transformed cells, the following procedure was used. A Fischer rat embryo cell line transformed by the Snyder-Theilen strain of feline sarcoma virus (ST-FeSV FRE clone-10), has previously been shown to produce elevated levels of rTGF (Gray et al. (1983) Nature 303, pp. 722–725). Serum-free conditioned medium was collected, processed and concentrated as described above. An aliquot of medium was then subjected to gel filtration chromatography on Bio-Gel P-10 under acidic conditions. Fractions were analyzed for rTGF by the EGF receptor competition assay or by RIA.

Two size classes of EGF-competing activity were detected under these conditions, one of approximate $M_r = 10,000$ and one of $M_r = 20.000$; both species eluted well behind the bulk of protein in the sample. Both size classes of EGF-competing activity also showed immunologic activity. Additional immunologic activity was found in the excluded volume of the column where no EGF-competing activity was detected. These findings indicate that previously described size classes of rTGF are active in the RIA. The ratio of EGF-competing to immunologic activity was greatly reduced in the high molecular weight TGF fractions, indicating that the biologic activities of these TGF(s) species are less than that of the low molecular weight fractions.

To confirm that the immunologic activity was carried by the same molecular species as EGF-competition activity, pooled fractions containing the $M_r = 10,000$ and $M_r = 20,000$ size classes of rTGF from a preparative scale version of this experiment were subjected to reverse phase chromatography on HPLC; conditions employed were similar to those used in the purification of rTGF as described in Marquardt et al. (1983) Proc. Natl. Acad. Sci. 80, pp. 4684–4688. For the $M_r = 10.000$ TGF pooled fractions, both EGF-competing and immunologic activity were shown to co-purify with essentially quantitative yields. The co-purification of both activities during both gel filtration chromatography and HPLC strongly suggested that both activities are carried by the same molecular species. When the $M_r = 20,000$ EGF-competition activity was subjected to HPLC, a similar co-purification of EGF-competing and immunologic activities was observed. These experiments indicate that the bulk of immunologic activity found in conditioned medium of ST-FeSV-FRE-clone 10 was due to rTGF.

Immunoblotting analysis of different size classes of rTGF

The larger size classes of TGFs found in conditioned medium from retroviral transformed rat cells could represent either aggregated states or distinct molecular forms of the TGF molecule. To distinguish between these alternatives, synthetic rTGF and both the $M_r = 10,000$ and $M_r = 20,000$ size classes of native TGF were subjected to immunoblotting analysis, following separation of component polypeptides by SDS-PAGE under reducing conditions. Immunoreactive synthetic rTGF and low molecular weight native rTGF co-migrated as single polypeptide chains of $M_r = 6,000$; immunologic reactivity of these molecules was blocked by incubation of antiserum with excess peptide III. In contrast, large molecular weight size class contained three immunoreacted peptides of $M_r = 24,000$, $M_r = 40,000$, and $M_r = 42,000$; immunologic reactivity of these peptides was also blocked by addition of excess peptide III. Another radioactive band having a migration of greater than $M_r = 43,500$ was noted in all lanes. This material was incompletely removed by inclusion of excess peptide III and was seen consistently in all experiments, regardless of the sample analyzed; therefore, it seems to represent an experimental artifact. It is noteworthy that no $M_r = 6,000$ TGF was detected in the large molecular weight size class. These results demonstrate that the higher molecular weight size classes of rTGF represent distinct forms of TGF.

EXAMPLE XII

Synthetic Fragment of rTGF with Receptor Binding and Antigenic Properties

Peptides

EGF was purified from mouse submaxillary glands by extraction with 1 M HCl containing 1% trifluoroacetic acid (TFA), 5% formic acid, and 1% NaCl, concentration on Sep-Pak columns (Waters), and reversed-phase high performance liquid chromatography on $\mu$Bondapak C-18 columns (Waters) as in Elson et al. (1984) Biochemistry Int. 8, pp. 427–435. The complete synthesis of native rat TGF has been described above in Example V.

The synthetic peptide fragments were prepared on chloromethyl-polystyrene-1% divinylbenzene resin (Bio-Rad) using Na-t-butoxycarbonyl protection. Peptides were deprotected and cleaved from the resin using HF or, for the analogs with blocked C-termini, the peptide was first removed by ammonolysis (NH$_3$/MeOH). The crude deprotected peptides were diluted and cyclized to the disulfide form by oxidation with 0.01 M K$_3$Fe(CN)$_6$. The peptide solution was loaded on a Bio-Rex 70 cation exchange column, washed with 300 mL of H$_2$O, and eluted with a gradient to 50% AcOH. The peptide was purified by prep-HPLC on a $2.5 \times 100$ cm column (Altex) of Vydac 218TP C-18 packing using approximately 20% CH$_3$CN eluent, 0.03 M in NH$_4$OAc at pH 4.5 (10). Peptides 1 and 2 represent the amino acid sequences 34 through 43 of rTGF with free or blocked (N-Ac; C-amide) ends, respectively. Peptide 3 is the methyl ester of the corresponding loop of hTGF (Ac-Cys-His-Ser-Gly-Tyr-Val-Gly-Ala-Arg-Cys-OMe) prepared by transesterification from the resin (base/MeOH).

Immunogen Preparation and Immunoassay

TGF peptide 1 was coupled to keyhole limpet hemocyanin (KLH) or bovine serum albumin (BSA) by thiol/maleimide linkage (King et al. (1979) *J. Immunol. Methods* 28, pp. 201–206). Carrier-peptide complexes were purified by gel filtration. An average of 60 moles peptide/mole KLH and 20 moles peptide/mole BSA was achieved. Rabbits were immunized with the KLH-peptide 1 conjugate by multiple subcutaneous (s.c.) and intramuscular (i.m.) injections of 2 mg protein in complete Freund's adjuvant. Rabbits were boosted s.c. every two weeks with the immunogen in incomplete Freund's adjuvant. The IgG fraction of the antiserum after 5 boosts was used for immunoassays and radiolabeled using $Na^{125}I$ (NEN) and Enzymobeads (Bio-Rad) to $4\times10^5$ cpm/$\mu$g protein. Polyvinyl chloride 96-well plates (Costar) were coated with 200 $\mu$g/mL BSA-peptide 1 conjugate and countercoated with 10% normal rabbit serum in phosphate-buffered saline. Plates were incubated for 4 hours at 37° C. with [$^{125}$I]anti-KLH-peptide 1 IgG (50,000 cpm/well) in the presence or absence of inhibitors, washed and individual wells were counted.

Radioreceptor Assay

A-431 human epidermoid carcinoma cells or human foreskin fibroblasts (HFF), established from primary cultures, were grown to confluence in 24-well cluster dishes (Costar) in Dulbecco's minimal essential medium (DMEM, Gibco) containing 10% fetal calf serum (FCS, Hyclone). EGF was radio-iodinated as above to between $4\times10^4$ and $8\times10^4$ cpm/ng protein. Cells were incubated at 4° C. for 60 minutes with 1 nM [$^{125}$I]EGF in the presence of inhibitor peptides in DMEM (pH 70.4; 20 mM Hepes) containing 0.1% BSA. Cells were washed 3× with cold buffer, lysed with 0.1 N NaOH, and cell-associated radioactivity was measured ($\gamma$-counter). Nonspecific binding assessed in the presence of a 100× excess of cold EGF was less than 5% and 10% of the specific binding for A-431 and HFF cells, respectively.

Cell Proliferation Assay

HFF cells were grown to confluence in 48-well cluster dishes in DMEM-10% FCS and brought to quiescence by starvation for 2 days in DMEM-0.5% FCS. Mitogens and peptides were incubated with cells at 37° C. for 18 hours prior to a 4 hour pulse with 1 $\mu$Ci [$^3$H]methyl-thymidine (NEN) and trichloroacetic acid precipitable radioactivity was determined.

Results

Rabbit antibodies against the KLH-peptide 1 conjugate reacted with BSA-TGF peptide by solid phase RIA. This reaction was inhibited in a concentration-dependent fashion by peptide 1 and slightly less by native TGF. In contrast, EGF did not cause significant inhibition.

Rat TGF competitively displaces the binding of EGF to its receptors. The ability of TGF peptides to compete with [$^{125}$I]EGF binding to either A-431 cells or HFF was evaluated. Peptide 1 partially inhibited [$^{125}$I]EGF binding to A-431 cells at $>10^{-6}$ M. Peptides 2 and 3, however, exhibited an improved binding inhibition, with $IC_{50}$'s of $4\times10^{-6}$ M and $4\times10^{-7}$ M, respectively (i.e., approximately 0.02 and 0.2% of the binding potency of EGF or TGF-$\alpha$). Similar observations were made for the inhibition of EGF on HFF (Table IX). The receptor specificity of these interactions is illustrated by the inability of these peptides to inhibit either the binding or mitogenic effect of Endothelial Cell Growth Factor on HFF (not shown).

None of the TGF peptides possessed intrinsic mitogenic properties up to $10^{-5}$ M when incubated with quiescent HFF (data not shown). However, the TGF peptides inhibited, in a concentration-dependent fashion, the induction of DNA synthesis in quiescent HFF by EGF. These antagonists were equally potent when TGF was used as mitogen (Table IX). As seen for the binding potency, the antagonistic potency of the TGF peptides was improved by capping of the amino- and carboxy-termini.

TABLE IX

| | Biological Activities of Synthetic TGF Fragments | | | |
|---|---|---|---|---|
| | Binding[a] $IC_{50}$ (M) | | Inhibition of Mitogenesis[b] $IC_{50}$ (M) | |
| | A-431 | HFF | EGF | TGF$\alpha$ |
| Peptide 1 | $8 \pm 2 \times 10^{-5}$ | $6 \pm 2 \times 10^{-5}$ | $>10^{-5}$ | $>10^{-5}$ |
| Peptide 2 | $4 \pm 2 \times 10^{-6}$ | $2 \pm 2 \times 10^{-6}$ | $5 \pm 2 \times 10^{-6}$ | $3 \pm 1 \times 10^{-6}$ |
| Peptide 3 | $4 \pm 1 \times 10^{-7}$ | $3 \pm 1 \times 10^{-7}$ | $6 \pm 2 \times 10^{-7}$ | $5 \pm 3 \times 10^{-7}$ |

[a] $IC_{50}$'s derived from inhibition curves for the binding of 1 nM [$^{125}$I]EGF to cells.
[b] $IC_{50}$'s are the concentrations that decrease by half the enhancement over control of [$^3$H]methyl-thymidine incorporation in quiescent HFF induced by 1 nM of EGF of TGF$\alpha$.

EXAMPLE XIII

TGF$\alpha$ Stimulates Bone Resorption in Vitro

Transforming growth factor preparations were purified from human melanoma cell conditioned medium and human platelets as described in Example I and synthetic rat TGF was prepared as previously described in Example II. Biological activity of the TGF preparations and synthetic TGF was monitored using an EGF radioreceptor assay or using the soft agar colony formation. also as described in Example I.

Synthetic rat TGF ($M_r=5600$) resorbed bone in a concentration dependent manner. Concentrations greater than 2 ng EGF equivalents/ml stimulated bone resorption in three separate experiments. The synthetic TGF required at least 72 hours to stimulate bone resorption. In this respect the synlhetic form appears similar to EGF which resorbs bone over a similar time course in this bioassay. (Tashjian et al. (1978) *Biochem. Biophys. Res. Commun.* 85. 966.)

Partially purified preparations of high and low molecular weight TGFs prepared from a human melanoma cell line were also tested in the bone resorption assay. Both high (27,000 daltons) and low (6,000 daltons) molecular weight forms stimulated bone resorption. The high molecular weight form stimulated resorption within 48 hours, while the low molecular weight form required 72–96 hours to stimulate resorption, a similar time course to that of synthetic rat TGF-I and EGF (See Tashjian, supra.)

The results show that TGF can stimulate bone resorption in vitro. Synthetic rat TGF and low molecular weight human TGF preparations behaved in a manner similar to that of EGF, since they required prolonged incubation periods to stimulate bone resorption. They were effective at concentrations of about one order of magnitude less than EGF. The high molecular weight human melanoma TGF stimulated bone resorption within 48 hours.

EXAMPLE XIV

Stimulation of Bone Resorption in Vitro by Synthetic Transforming Growth Factor

Synthetic rat TGF was prepared as described above in Example V. Purity of the protein was confirmed by sodium dodecyl sulfate-polyacrylamide gel electrophoresis, amino acid analysis, and reverse phase high-performance liquid chromatography. The biological activity of TGF preparations and synthetic TGF was monitored by means of an EGF radioreceptor assay. (Todaro et al. (1976) *Nature* 264, 26.) Bone resorption was assessed by measuring the release of $^{45}$Ca from previously labeled fetal rat long bones. Pregnant rats at the 18th day of gestation were injected with 200 μCi of $^{45}$Ca. (Raisz (1975) *J. Clin. Invest.* 44, 103.) The mothers were killed on the 19th day of gestation, and the fetuses were removed. The mineralized shafts of the radii and ulnae were dissected free of surrounding tissue and cartilage and placed in organ culture. The bones were incubated in BGJb medium (Irvine Scientific) for 24 hours at 37° C. in a humidified atmosphere of 5 percent of $CO_2$ and 95 percent air to allow for the exchange of loosely complexed $^{45}$Ca. The bones were then cultured for 48 to 120 hours in BGJb medium supplemented with 5 percent fetal calf serum (KC Biologicals) containing control or test substances. Bone-resorbing activity was measured as the percentage of total $^{45}$Ca released into the medium and was expressed as a treated-to-control ratio. Statistical significance was determined with Student's t test for unpaired data.

Synthetic rat TGF (molecular weight, 5600) in concentrations greater than 2 ng of EGF equivalents per milliliter stimulated bone resorption in a concentration-dependent manner in three separate experiments. Synthetic TGF caused no significant bone resorption during the first 48 hours of bone culture. but clearly stimulated resorption over the following 3 days. In this respect the synthetic form of TGF appears to be similar to EGF, which resorbs bone over a similar time course in this bioassay. (Raisz et al. (1980) *Endocrinology* 107, 270.) The effect of TGF on bone resorption appeared to be independent of prostaglandin synthesis.

Since rat TGF resorbed bone in vitro, human preparations containing TGF activity were also tested for their effects on bone. Partially purified preparations of high and low molecular weight TGF were prepared from a human melanoma cell line. (Marquardt et al. (1982) *J. Biol. Chem.* 275, 5220.) These preparations were partially purified by acid extraction and gel filtration chromatography. Both high (13,000) and low (6,000) molecular weight forms stimulated bone resorption. The high molecular weight form stimulated resorption within 48 hours, whereas the low molecular weight form required 72 to 96 hours to stimulate resorption—a time course similar to that of synthetic rat TGF and EGF.

EXAMPLE XV

Vaccinia Virus Infected Cells Release a Novel Polypeptide Functionally Related to Transforming and Epidermal Growth Factors Cell Culture and Virus Cercopithecus monkey kidney (BSC-1) cell monolayers were maintained in Eagles basal medium supplemented with 10% fetal calf serum. Vaccinia virus (VV) (strain WR) was grown in Hela cells and purified by sucrose density gradient sedimentation. (Moss (1981) *In Gene Amplification and Analysis,* Vol. 2, eds., Chirickjian and Papis (Elsevier/North Holland, New York pp. 253–266.)

Preparation of Conditioned Medium

BSC-1 cell monolayers were incubated at 37° C. with purified virus in Eagles basal medium supplemented with 2% fetal calf serum. Cell culture supernatants were clarified by low speed centrifugation and lyophilized. The residue was then resuspended in 1 M acetic acid and dialyzed extensively against 0.2 M acetic acid. Insoluble material was removed by centrifugation and the supernatant was lyophilized and resuspended in one-hundredth of the original volume of 1 M acetic acid and stored at 4° C.

Chromatography

Gel filtration was performed on columns of Bio-Gel P-10 (BioRad, Richmond, Calif.) equilibrated in 1 M acetic acid. Sizing on high pressure liquid chromatography system utilized two Bio-Sil TSK-250 columns (BioRad) in series.

The material isolated, designated as Vaccinia virus growth factor (VGF), possessed the amino acid sequence given in Example VI above.

Radioreceptor Assay

The Radioreceptor assay used was similar to the one described above in Example I. TGF and VGF concentrations were expressed as the amount required to produce an inhibition of $^{125}$I-EGF binding equivalent to a known amount of EGF.

Radioimmunoassay

The Radioimmunoassay used was similar to the one described above in Example XI.

Results

Presence of EGF-Competing Activity in the Culture Medium of VV Infected Cells

The supernatant, derived from BSC-1 cell 24 hr after infection with VV, was tested for the presence of material that could compete with $^{125}$I-labeled EGF for binding to EGF receptor-rich human epidermoid carcinoma cells (A431). VV infected cells released a potent EGF competing activity which essentially saturates (>10 ng) the assay with the equivalent of 10 ng of material resuspended from 0.5 ml of culture fluid. The activity was designated VV growth factor (VGF). (In contrast, mock infected BSC-1 control cultures contained minimal EGF competing activity even at the lowest dilution tested.)

The next experiments were designed to examine the kinetics of VGF production. At the earliest time examined, 2 hr after infection, enhanced levels of EGF competing activity already were present in the culture medium suggesting rapid synthesis and release of VGF. By 12 hr, maximal amounts of this activity were found in culture supernatants; only a slight increase was noted at 24 hr. Since the VV encoded polypeptide with structural homology to EGF and TGF is an early gene product, VGF expression was monitored in BSC-1 cell cultures treated with cytosine arabinoside (AraC) starting immediately after the 1 hr virus adsorption period. Inhibition of DNA synthesis by AraC blocks the expression of late vaccinia genes, whereas early gene products are not similarly affected. VGF production was not inhibited in AraC treated cultures but, relative to infected control cultures, was enhanced more than two-fold at 13 and 24 hr post infection. The level of VGF production was also a function of the virus inoculum (Table XI). With a plaque forming unit (PFU) to cell ratio of 20:1, approximately 3 ng EGF equivalents of VGF per ml were detected in culture supernatants at 24 hr post infection. VGF production was proportional to multiplicity of infection, with about 6 and 10 ng equivalents of EGF detected in BSC-1 cultures infected at ratios of 40 and 80 PFU/cell respectively.

TABLE XI

EFFECT OF MULTIPLICITY OF INFECTION ON VGF RELEASE

| Virus Multiplicity PFU/cell | VGF Released ng Eq. of EGF/ml |
|---|---|
| 0 | — |
| 10 | 2.7 |
| 20 | 4.5 |
| 40 | 6.1 |
| 80 | 10.0 |

Partial Purification of VGF

The EGF-competing activity found in VV infected BAS-1 cells was partially purified from acid extracted culture supernatants at 24 hr post infection. Acid solubilized polypeptides (10.5 mg) from VV infected cell culture supernatants were applied to a Bio-Gel P-10 column equilibrated in 1 M acetic acid and samples of each fraction were tested for EGF competing activity. The major peak of EGF competition (fraction 42) eluted, slightly after the $M_r = 29,000$ carbonic anhydrase marker, with an apparent molecular weight of 25,000. No significant activity was detected in fractions corresponding to the known elution position of EGF (fraction 100) or rat TGF (fraction 78) on this column. Peak VGF activity (fraction 42-44) was used for subsequent biological studies. The molecular weight was confirmed utilizing tandemly-linked Bio-Sil TSK 250 HPLC sizing columns. All of the EGF competing activity eluted as a major peak in the region of the $M_r = 25,000$ protein marker.

Immunological Comparison of EGF and TGF

To further compare TGF with VGF, the latter was tested in competitive radioimmunoassay for TGF as described above. The assay can distinguish EGF from TGF and recognizes both low and high molecular weight forms of TGF of rat and human origin. (Linsley et al. (1985) *Proc. Natl. Acad. Sci. USA* 82, pp. 365–369.) Rat TGF effectively competed with $^{125}$I-labeled TGF peptide for binding to antibody with a slope similar to that of unlabeled TGF peptide. A 50% displacement of antigen from antibody was observed at an antigen concentration of approximately 0.2–0.3 ng equivalents of EGF. When VGF was tested at equivalent concentrations, no competition was observed, suggesting that VGF is not a member of the TGF family of peptides, insofar as immunological properties are concerned. In a competitive radioimmunoassay for native EGF, VGF preparations exhibited a minimal displacement ($>10\%$) of $^{125}$I-labeled EGF from a polyclonal antibody to native EGF.

Biological Activity of VGF

At least an order of magnitude more VGF ($>2000$ ng/l) was found relative to the highest TGF producer, Fisher rat embryo cells (FRE) non-productively transformed by Snyder-Theilen Feline sarcoma virus.

In a TGF dependent soft agar assay for anchorage independent cell growth. VGF stimulated normal rat kidney cells to form progressively growing colonies in soft agar. On a ng equivalent basis, partially purified VGF preparations produced 102 colonies whereas EGF and rat TGF produced 120 and 154 colonies respectively. (It is possible that contaminating activities in partially purified VGF preparations may influence quantitation in this type of biological assay.)

VGF also exhibited potent mitogenicity when tested on a variety of cultured fibroblasts. When tested at equivalent EGF receptor binding levels with serum starved (48 hours) mink fibroblasts (which have relatively high numbers of EGF membrane receptor sites), VGF elicited a 78% increase in DNA synthesis relative to unstimulated serum deprived cells, whereas a 59% stimulation in deoxyuridine incorporation was seen with mouse submaxillary gland EGF. Thus the mitogenic effect of VGF is at least as strong as that of EGF.

What is claimed is:

1. A method of promoting repair of tissue damage in a human host which comprises administering to the locus of said tissue damage in said human host an effective amount of a biologically active polypeptide containing at least one peptide sequence of formula:

$$-\text{Cys}-(\text{AA})_a-\text{Cys}-(\text{AA})_b-\text{Cys}-(\text{AA})_c-$$
$$\quad\; 1 \qquad\qquad 2 \qquad\qquad 3$$

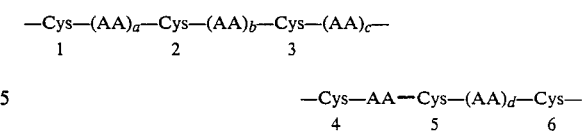

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10 and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

2. A composition for treatment of cancer or other proliferative disease which comprises a therapeutic amount of a polypeptide transforming growth factor or oligomer thereof of the formula:

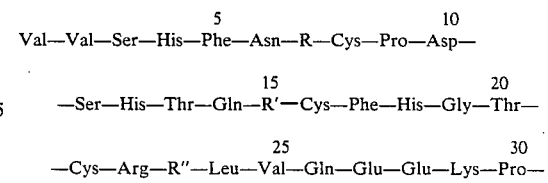

-continued

—Ala—Cys—Val—Cys—His—Ser—Gly—R'''—Val—Gly— (35-40)

—Val—Arg—Cys—Glu—His—Ala—Asp—Leu—Leu—Ala (45-50)

wherein R is Asp or Lys, R' is Phe or Tyr, R" is Ser or Phe and R''' is Phe or Tyr together with a pharmaceutically acceptable carrier therefor.

3. A composition for treatment of tissue damage which comprises an effective amount of a polypeptide containing at least one peptide sequence of formula:

—Cys—(AA)$_a$—Cys—(AA)$_b$—Cys—(AA)$_c$—
  1         2         3

—Cys—AA—Cys—(AA)$_d$—Cys—
  4      5       6 wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8 together with a pharmaceutically acceptable carrier therefor, wherein the polypeptide is capable of binding to the EGF receptor, has a molecular weight from about 5,000 to about 35,000, and Cys-1 is bonded to Cys-3, Cys-2 is bonded to Cys-4, and Cys-5 is bonded to Cys-6 through disulfide bonds.

4. A method for treating a human host suspected of having malignant cells which comprises administering to said human host an antibody raised to a polypeptide transforming growth factor or oligomer thereof of the formula:

Val—Val—Ser—His—Phe—Asn—R—Cys—Pro—Asp— (5-10)

—Ser—His—Thr—Gln—R'—Cys—Phe—His—Gly—Thr— (15-20)

—Cys—Arg—R"—Leu—Val—Gln—Glu—Asp—Lys—Pro— (25-30)

—Ala—Cys—Val—Cys—His—Ser—Gly—R'''—Val—Gly— (35-40)

—Ala—Arg—Cys—Glu—His—Ala—Asp—Leu—Leu—Ala (45-50)

wherein R is Asp or Lys, R' is Phe or Tyr, R" is Ser or Phe and R''' is Phe or Tyr in a therapeutic amount.

5. A method for treating a human host suspected of having malignant cells which comprises administering to said human host an antibody raised to a transforming growth factor polypeptide in a therapeutic amount wherein the polypeptide is capable of transforming non-neoplastic cells by causing the:
 (a) loss of density-dependent inhibition of cell growth in monolayer culture;
 (b) overgrowth of cells in monolayer culture;
 (c) change in cellular shape, with the result that the cells assume the neoplastic phenotype; and
 (d) which contains at least one peptide sequence of formula:

—Cys—(AA)$_a$—Cys—(AA)$_b$—Cys—(AA)$_c$—
  1         2         3

—Cys—AA—Cys—(AA)$_d$—Cys—
  4      5       6 wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein Cys-1 is bonded to Cys-3, Cys-2 is bonded to Cys-4 and Cys-5 is bonded to Cys-6 through disulfide bonds, the polypeptide is capable of binding to the EGF receptor, and its molecular weight is from about 5,000 to about 35,000.

6. A method for treating a human host suspected of having malignant cells which comprises administering to said human host an antibody raised to a biologically active polypeptide containing at least one peptide sequence of the formula:

—Cys—(AA)$_a$—Cys—(AA)$_b$—Cys—(AA)$_c$—
  1         2         3

—Cys—AA—Cys—(AA)$_d$—Cys—
  4      5       6 wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8 in a therapeutic amount, wherein the polypeptide is capable of binding to the EGF receptor, has a molecular weight from about 5,000 to about 35,000, and Cys-1 is bonded to Cys-3, Cys-2 is bonded to Cys-4, and Cys-5 is bonded to Cys-6 through disulfide bonds.

7. A method for treating a human host suspected of having malignant cells which comprises administering to said human host an antibody raised to a biologically active polypeptide or oligomer thereof of the formula:

(AA)$_n$—Cys—(AA)$_m$—Cys—(AA)$_o$—Cys—(AA)$_p$—Cys—AA—Cys—(AA)$_q$—Cys—(AA)$_r$
      1         2         3         4      5       6 wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12 in a therapeutic amount, wherein the polypeptide is capable of binding to the EGF receptor, has a molecular weight from about 5,000 to about 35,000 and Cys-1 is bonded to Cys-3, Cys-2 is bonded to Cys-4 and Cys-5 is bonded to Cys-6 through disulfide bonds.

8. A method for treating a human host suspected of having malignant cells which comprises administering to said human host an antibody raised to a biologically active polypeptide containing at least one peptide sequence of the formula:

—Cys—(AA)$_a$—Cys—(AA)$_b$—Cys—(AA)$_c$—
  1         2         3

—Cys—AA—Cys—(AA)$_d$—Cys—
  4      5       6 wherein AA is an amino acid residue selected from Val, Ser, His, Phe, Ile, Met, Asn, Lys, Asp, Thr, Gln, Arg, Leu, Glu, Pro, Ala, Gly, Trp and Tyr, and a is 7, b is 4, c is 10, and d is 8 in a therapeutic amount, wherein the polypeptide is capable of binding to the EGF receptor, has a molecular weight from about 5,000 to about 35,000, and Cys-1 is bonded to Cys-3, Cys-2 is bonded to Cys-4, and Cys-5 is bonded to Cys-6 through disulfide bonds.

9. A method for treating a human host suspected of having malignant cells which comprises administering to said human host an antibody raised to a biologically active polypeptide or oligomer thereof of the formula:

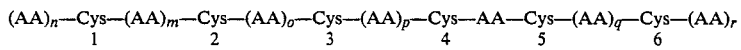

wherein AA is an amino acid residue selected from Val, Ser, Ile, Met, His, Phe, Asn, Lys, Asp, Thr, Gln, Arg, Leu, Glu, Pro, Ala, Gly, Trp and Tyr, and n is an integer of from 4 to 10, m is 7, o is 4, p is 10, q is 8 and r is an integer of from 6 to 12 in a therapeutic amount, wherein the polypeptide is capable of binding to the EGF receptor, has a molecular weight from about 5,000 to about 35,000 and Cys-1 is bonded to Cys-3, Cys-2 is bonded to Cys-4 and Cys-5 is bonded to Cys-6 through disulfide bonds.

10. The method of claim 5, 6, 7, 8, or 9 wherein the antibody is labeled with a cytotoxic agent.

11. A method for treating a human host suspected of having malignant cells which comprises administering to said human host an antibody raised to a polypeptide growth factor containing one or more of the following peptide sequences:
A. Val-Val-Ser-His-Phe-Asn-Lys-Cys-Pro-Asp-Ser-His-Thr-Gln-Tyr-Cys-Phe-His-Gly-Thr-Cys
B. Val-Val-Ser-His-Phe-Asn-Asp-Cys-Pro-Asp-Ser-His-Thr-Gln-Phe-Cys-Phe-His-Gly-Thr-Cys
C. Leu-Val-Gln-Glu-Glu-Lys-Pro-Ala-Cys-Val-Cys-His-Ser-Gly
D. Cys-His-Ser-Gly-Tyr-Val-Gly-Val-Arg-Cys-Glu-His-Ala-Asp-Leu-Leu-Ala
E. Leu-Val-Gln-Glu-Asp-Lys-Pro-Ala-Cys-Val-Cys-His-Ser-Gly and
F. Cys-His-Ser-Gly-Tyr-Val-Gly-Ala-Arg-Cys-Glu-His-Ala-Asp-Leu-Leu-Ala
in a therapeutic amount.

12. A method for treating a human host suspected of having malignant cells which comprises administering to said human host an antibody raised to an antigeneic polypeptide selected from the sequences consisting of:
A. Val-Val-Ser-His-Phe-Asn-Asp-Cys-Pro-Asp-His-Thr
B. Val-Val-Ser-His-Phe-Asn-Lys-Cys-Pro-Asp-His-Thr
C. Arg-Phe-Leu-Val-Gln-Glu-Glu-Lys-Pro-Ala
D. Arg-Tyr-Leu-Val-Gln-Glu-Glu-Lys-Pro-Ala
E. Cys-His-Ser-Gly-Phe-Val-Gly-Val-Arg-Cys-Glu-His-Ala-Asp-Leu-Leu-Ala
F. Cys-His-Ser-Gly-Tyr-Val-Gly-Val-Arg-Cys-Glu-His-Ala-Asp-Leu-Leu-Ala
G. Arg-Phe-Leu-Val-Gln-Glu-Asp-Lys-Pro-Ala
H. Arg-Tyr-Leu-Val-Gln-Glu-Asp-Lys-Pro-Ala
I. Cys-His-Ser-Gly-Phe-Val-Gly-Ala-Arg-Cys-Glu-His-Ala-Asp-Leu-Leu-Ala
J. Cys-His-Ser-Gly-Tyr-Val-Gly-Ala-Arg-Cys-Glu-His-Ala-Asp-Leu-Leu-Ala
K. Val-Val-Ser-His-Phe-Asn-Asp-Cys-Pro-Asp-Ser-His-Thr and
L. Val-Val-Ser-His-Phe-Asn-Lys-Cys-Pro-Asp-Ser-His-Thr
in a therapeutic amount.

13. A method for treating a human host suspected of having malignant cells which comprises administering to said human host an antibody raised to a polypeptide selected from the sequences consisting of:
(1) Cys-His-Ser-Gly-Tyr-Val-Gly-Val-Arg-Cys
(2) Cys-His-Ser-Gly-Phe-Val-Gly-Val-Arg-Cys
(3) Cys-His-Ser-Gly-Tyr-Val-Gly-Ala-Arg-Cys
(4) Cys-His-Ser-Gly-Phe-Val-Gly-Ala-Arg-Cys and
(5) Cys-Ser-His-Gly-Tyr-Thr-Gly-Ile-Arg-Cys
in a therapeutic amount.

14. The method of claim 11, 12, or 13 wherein the antibody is labeled with a cytotoxic agent.

15. The method of claim 4 wherein R is Asp, R' is Phe, R" is Phe and R'" is Tyr.

16. A method for treating a human host suspected of having malignant cells which comprises administering to said human host an antibody raised to a polypeptide wherein the polypeptide contains one or more of the following peptide sequences:
A. Val-Val-Ser-His-Phe-Asn-Lys-Cys-Pro-Asp-Ser-His-Thr-Gln-Tyr-Cys-Phe-His-Gly-Thr-Cys
B. Val-Val-Ser-His-Phe-Asn-Asp-Cys-Pro-Asp-Ser-His-Thr-Gln-Phe-Cys-Phe-His-Gly-Thr-Cys
C. Leu-Val-Gln-Glu-Glu-Lys-Pro-Ala-Cys-Val-Cys-His-Ser-Gly
D. Cys-His-Ser-Gly-Thr-Val-Gly-Val-Arg-Cys-Glu-His-Ala-Asp-Leu-Leu-Ala
E. Leu-Val-Gln-Glu-Asp-Lys-Pro-Ala-Cys-Val-Cys-His-Ser-Gly and
F. Cys-His-Ser-Gly-Tyr-Val-Gly-Ala-Arg-Cys-Glu-His-Ala-Asp-Leu-Leu-Ala
in a therapeutic amount.

17. A method for treating a human host suspected of having malignant cells which comprises administering to said human host an antibody raised to a polypeptide wherein the polypeptide contains one or more of the following peptide sequences:
A. Val-Val-Ser-His-Phe-Asn-Aap-Cys-Pro-Asp-His-Thr
B. Val-Val-Ser-His-Phe-Asn-Lys-Cys-Pro-Asp-His-Thr
C. Arg-Phe-Leu-Val-Gln-Glu-Glu-Lys-Pro-Ala
D. Arg-Tyr-Leu-Val-Gln-Glu-Glu-Lys-Pro-Ala
E. Cys-His-Ser-Gly-Phe-Val-Gly-Val-Arg-Cys-Glu-His-Ala-Asp-Leu-Leu-Ala
F. Cys-His-Ser-Gly-Tyr-Val-Gly-Val-Arg-Cys-Glu-His-Ala-Asp-Leu-Leu-Ala
G. Arg-Phe-Leu-Val-Gln-Glu-Asp-Lys-Pro-Ala
H. Arg-Tyr-Leu-Val-Gln-Glu-Asp-Lys-Pro-Ala
I. Cys-His-Ser-Gly-Phe-Val-Gly-Ala-Arg-Cys-Glu-His-Ala-Asp-Leu-Leu-Ala
J. Cys-His-Ser-Gly-Tyr-Val-Gly-Ala-Arg-Cys-Glu-His-Ala-Asp-Leu-Leu-Ala
K. Val-Val-Ser-His-Phe-Asn-Asp-Cys-Pro-Asp-Ser-His-Thr and
L. Val-Val-Ser-His-Phe-Asn-Lys-Cys-Pro-Asp-Ser-His-Thr
in a therapeutic amount.

18. The method of claim 4, 14, 15 or 16 wherein the antibody is labled with a cytotoxic agent.

19. A method for treating a host suspected of having malignant cells which comprises administering to said host an antibody raised to a biologically active polypeptide containing at least one peptide sequence of formula:

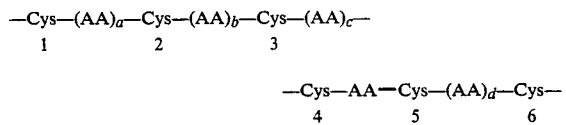

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8 in a therapeutic amount, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

20. A method for treating a host suspected of having malignant cells which comprises administering to said host an antibody raised to a biologically active polypeptide or oligomer thereof of the formula:

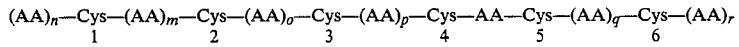

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12 in a therapeutic amount, wherein the polypeptide is capable of binding to the EGF receptor, has a molecular weight from about 5,000 to about 35,000 and Cys-1 is bonded to Cys-3, Cys-2 is bonded to Cys-4 and Cys-5 is bonded to Cys-6 through disulfide bonds.

21. A method for treating a host suspected of having malignant cells which comprises administering to said host an antibody raised to a biologically active polypeptide containing at least one peptide sequence of the formula:

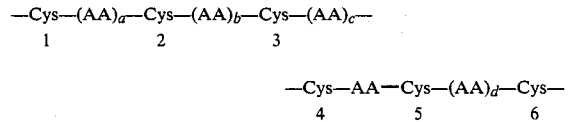

wherein AA is an amino acid residue selected from Val, Ser, His, Phe, Ile, Met, Asn, Lys, Asp, Thr, Gln, Arg, Leu, Pro, Ala, Gly, Trp and Tyr, and a is 7, b is 4, c is 10, and d is 8 in a therapeutic amount, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

22. The method of claim 19, 20, or 21 wherein the antibody is labeled with a cytotoxic agent.

23. A method for treating or aiding in the treatment of a human host diagnosed as having cancer or other proliferative disease which comprises administering to said human host an effective amount of a transforming growth factor polypeptide wherein the polypeptide is capable of transforming non-neoplastic cells by causing the:

(a) loss of density-dependent inhibition of cell growth in monolayer culture;
(b) overgrowth of cells in monolayer culture;
(c) change in cellular shape, with the result that the cells assume the neoplastic phenotype; and
(d) which contains at least one peptide sequence of formula:

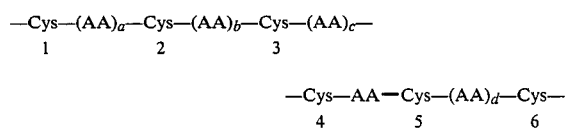

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein Cys-1 is bonded to Cys-3, Cys-2 is bonded to Cys-4 and Cys-5 is bonded to Cys-6 through disulfide bonds, the polypeptide is capable of binding to the EGF receptor, and its molecular weight is from about 5,000 to about 35,000.

24. A method for treating or aiding in the treatment of a human host diagnosed as having cancer or other proliferative disease which comprises administering to said human host an effective amount of a biologically active polypeptide containing at least one peptide sequence of formula:

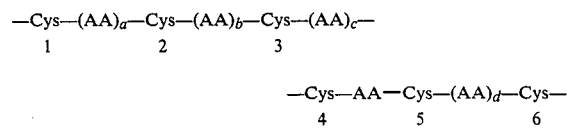

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

25. A method for treating or aiding in the treatment of a human host diagnosed as having cancer or other proliferative disease which comprises administering to said human host an effective amount of a biologically active polypeptide or oligomer thereof of the formula:

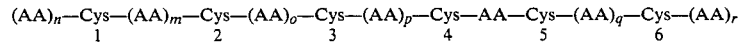

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

26. A method for treating or aiding in the treatment of a human host diagnosed as having cancer or other proliferative disease which comprises administering to said human host an effective amount of a biologically active polypeptide containing at least one peptide sequence of the formula:

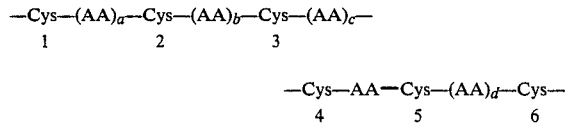

wherein AA is an amino acid residue selected from Val, Ser, His, Phe, Ile, Met, Asn, Lys, Asp, Thr, Gln, Arg, Leu, Glu, Pro, Ala, Gly, Trp and Tyr, and a is 7, b is 4, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

27. A method for treating or aiding in the treatment of a human host diagnosed as having cancer or other proliferative disease which comprises administering to said human host an effective amount of biological active polypeptide or oligomer thereof of the formula:

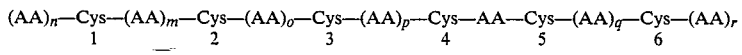

wherein AA is an amino acid residue selected from Val, Ser, Ile, Met, His, Phe, Asn, Lys, Asp, Thr, Gln, Arg, Leu, Glu, Pro, Ala, Gly, Trp and Tyr, and n is an integer of from 4 to 10, m is 7, o is 4, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

28. A method for treating or aiding in the treatment of a human host diagnosed as having cancer or other proliferative disease which comprises administering to said human host an effective amount of a polypeptide transforming growth factor or oligomer thereof of the formula:

$$\overset{5}{\text{Val—Val—Ser—His—Phe—Asn—R—Cys—Pro—Asp—}}^{10}$$

$$\overset{15}{\text{—Ser—His—Thr—Gln—R'—Cys—Phe—His—Gly—Thr—}}^{20}$$

$$\overset{25}{\text{—Cys—Arg—R''—Leu—Val—Gln—Glu—Glu—Lys—Pro—}}^{30}$$

$$\overset{35}{\text{—Ala—Cys—Val—Cys—His—Ser—Gly—R'''—Val—Gly—}}^{40}$$

$$\overset{45}{\text{—Val—Arg—Cys—Glu—His—Ala—Asp—Leu—Leu—Ala}}^{50}$$

wherein R is Asp or Lys, R' is Phe or Tyr, R'' is Ser or Phe and R''' is Phe or Tyr.

29. A method for treating or aiding in the treatment of a human host diagnosed as having cancer or other proliferative disease which comprises administering to said human host an effective amount of a polypeptide transforming growth factor or oligomer thereof of the formula:

$$\overset{5}{\text{Val—Val—Ser—His—Phe—Asn—R—Cys—Pro—Asp—}}^{10}$$

$$\overset{15}{\text{—Ser—His—Thr—Gln—R'—Cys—Phe—His—Gly—Thr—}}^{20}$$

$$\overset{25}{\text{—Cys—Arg—R''—Leu—Val—Gln—Glu—Asp—Lys—Pro—}}^{30}$$

$$\overset{35}{\text{—Ala—Cys—Val—Cys—His—Ser—Gly—R'''—Val—Gly—}}^{40}$$

$$\overset{45}{\text{—Ala—Arg—Cys—Glu—His—Ala—Asp—Leu—Leu—Ala}}^{50}$$

wherein R is Asp or Lys, R' is Phe or Tyr, R'' is Ser or Phe and R''' is Phe or Tyr.

30. A method for treating or aiding in the treatment of a host diagnosed as having cancer or other proliferative disease which comprises administering to said host an effective amount of a biologically active polypeptide containing at least one sequence of formula:

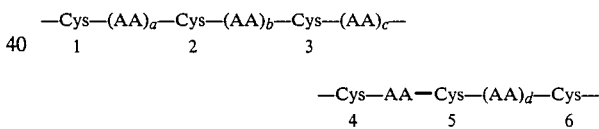

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein the polypeptide is capable of binding to the EGF receptor, has a molecular weight from about 5,000 to about 35,000 and Cys -1 is bonded to Cys-3, Cys-2 is bonded to Cys-4, and Cys-5 is bonded to Cys-6 through disulfide bonds.

31. A method for treating or aiding in the treatment of a host diagnosed as having cancer or other proliferative disease which comprises administering to said host an effective amount of a biologically active polypeptide or oligomer thereof of the formula:

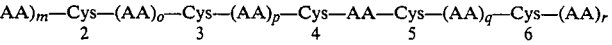

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

32. A method for treating or aiding in the treatment of a host diagnosed as having cancer or other proliferative disease which comprises administering to said host an effective amount of a biologically active polypeptide containing at least one peptide sequence of the formula:

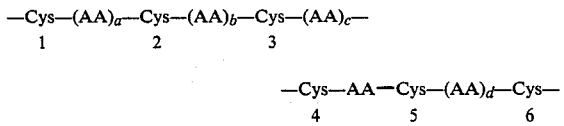

wherein AA is an amino acid residue selected from Val, Ser, His, Phe, Ile, Met, Asn, Lys, Asp, Thr, Gln, Arg, Leu, Glu, Pro, Ala, Gly, Trp and Tyr, and a is 7, b is 4, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

33. A method of promoting repair of tissue damage in a human host which comprises administering to the locus of said tissue damage in said human host an effective amount of a transforming growth factor polypeptide wherein the polypeptide is capable of transforming non-neoplastic cells by causing the:

(a) loss of density-dependent inhibition of cell growth in monolayer culture;
(b) overgrowth of cells in monolayer culture;
(c) change in cellular shape, with the result that the cells assume the neoplastic phenotype; and
(d) which contains at least one peptide sequence of formula:

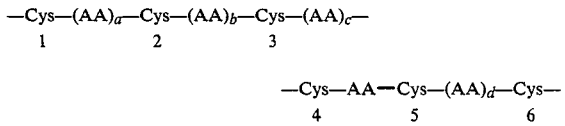

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein Cys-1 is bonded to Cys-3, Cys-2 is bonded to Cys-4 and Cys-5 is bonded to Cys-6 through disulfide bonds, the polypeptide is capable of binding to the EGF receptor, and its molecular weight is from about 5,000 to about 35,000.

34. A method of promoting repair of tissue damage in a human host which comprises administering to the locus of said tissue damage in said human host an effective amount of a biologically active polypeptide or oligomer thereof of the formula:

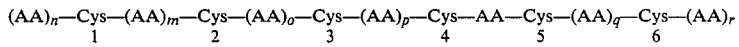

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

35. A method of promoting repair of tissue damage in a human host which comprises administering to the locus of said tissue damage in said human host an effective amount of a biologically active polypeptide containing at least one peptide sequence of the formula:

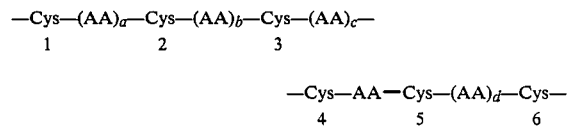

wherein AA is an amino acid residue selected from Val, Ser, His, Phe, Ile, Met, Asn, Lys, Asp, Thr, Gln, Arg, Leu, Glu, Pro, Ala, Gly, Trp and Tyr, and a is 7, b is 4, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

36. A method of promoting repair of tissue damage in a human host which comprises administering to the locus of said tissue damage in said human host an effective amount of a biologically active polypeptide or oligomer thereof of the formula:

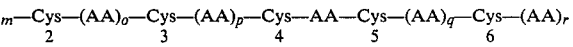

wherein AA is an amino acid residue selected from Val, Ser, Ile, Met, His, Phe, Asn, Lys, Asp, Thr, Gln, Arg, Leu, Glu, Pro, Ala, Gly, Trp and Tyr, and n is an integer of from 4 to 10, m is 7, o is 4, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

37. A method of promoting repair of tissue damage in a human host which comprises administering to the locus of said tissue damage in said human host an effective amount of a polypeptide transforming growth factor or oligomer thereof of the formula:

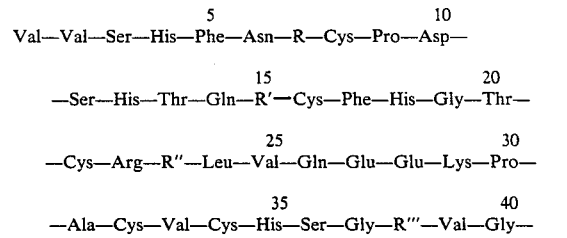

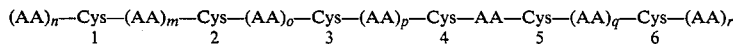

wherein R is Asp or Lys, R' is Phe or Tyr, R" is Ser or Phe and R'" is Phe or Tyr.

38. A method of promoting repair of tissue damage in a human host which comprises administering to the locus of said tissue damage in said human host an effective amount of a polypeptide transforming growth factor or oligomer thereof of the formula:

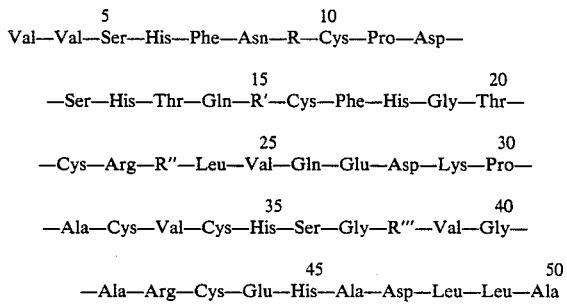

wherein R is Asp or Lys, R' is Phe or Tyr, R" is Ser or Phe and R''' is Phe or Tyr.

39. A method of promoting repair of tissue damage in a host which comprises administering to the locus of said tissue damage in said host an effective amount of a biologically active polypeptide containing at least one peptide sequence of formula:

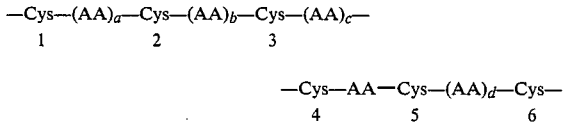

wherein AA is an amino acid residue selected from Val, Ser, His, Phe, Asn, Lys, Asp, Thr, Gln, Arg, Leu, Glu, Pro, Ala, Gly, Trp and Tyr, and a is 7, b is 4 or 5, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

40. A method of promoting repair of tissue damage in a host which comprises administering to the locus of said tissue damage in said host an effective amount of a biologically active polypeptide or oligomer thereof of the formula:

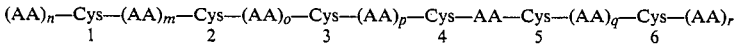

wherein AA is an amino acid residue selected from Val, Ser, His, Phe, Asn, Lys, Asp, Thr, Gln, Arg, Leu, Glu, Pro, Ala, Gly, Trp and Tyr, and n is an integer of from 4 to 10, m is 7, o is 4 or 5, p is 10, q is 8 and r is an integer of from 6 to 12, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

41. A method of promoting repair of tissue damage in a host which comprises administering to the locus of said tissue damage in said host an effective amount of a biologically active polypeptide containing at least one peptide sequence of the formula:

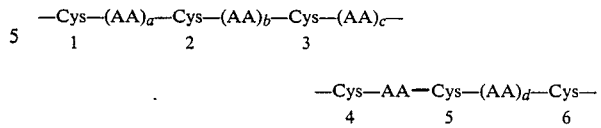

wherein AA is an amino acid residue selected from Val, Ser, His, Phe, Ile, Met, Asn, Lys, Asp, Thr, Gln, Arg, Leu, Glu, Pro, Ala, Gly, Trp and Tyr, and a is 7, b is 4, c is 10, and d is 8, wherein the polypeptide is capable of binding to the EGF receptor, has a molecular weight from about 5,000 to about 35,000 and Cys-1 is bonded to Cys-3, Cys-2 is bonded to Cys-4, and Cys-5 is bonded to Cys-6 through disulfide bonds.

42. A composition for treatment of cancer or other proliferative disease which comprises a therapeutic amount of an antibody raised to a polypeptide of the formula:

$$\text{Val—Val—Ser—His—Phe—Asn—R—Cys—Pro—Asp—}$$
$$\text{—Ser—His—Thr—Gln—R'—Cys—Phe—His—Gly—Thr—}$$
$$\text{—Cys—Arg—R''—Leu—Val—Gln—Glu—Asp—Lys—Pro—}$$
$$\text{—Ala—Cys—Val—Cys—His—Ser—Gly—R'''—Val—Gly—}$$
$$\text{—Ala—Arg—Cys—Glu—His—Ala—Asp—Leu—Leu—Ala}$$

wherein R is Asp or Lys, R' is Phe or Tyr, R" is Ser or Phe and R''' is Phe or Tyr, together with a pharmaceutically acceptable carrier therefor.

43. A method for treating a human host suspected of having malignant cells which comprises administering to said human host an antibody raised to a polypeptide transforming growth factor or oligomers thereof of the formula:

$$\text{Val—Val—Ser—His—Phe—Asn—R—Cys—Pro—Asp—}$$
$$\text{—Ser—His—Thr—Gln—R'—Cys—Phe—His—Gly—Thr—}$$
$$\text{—Cys—Arg—R''—Leu—Val—Gln—Glu—Glu—Lys—Pro—}$$
$$\text{—Ala—Cys—Val—Cys—His—Ser—Gly—R'''—Val—Gly—}$$
$$\text{—Val—Arg—Cys—Glu—His—Ala—Asp—Leu—Leu—Ala}$$

wherein R is Asp or Lys, R' is Phe or Tyr, R" is Ser or Phe and R''' is Phe or Tyr in a therapeutic amount.

44. The method of claim 43 wherein the antibody is labeled with a cytotoxic agent.

* * * * *